US006535796B1

(12) United States Patent
Sierro et al.

(10) Patent No.: US 6,535,796 B1
(45) Date of Patent: Mar. 18, 2003

(54) METHOD FOR CHARACTERIZING COMPLEX FLUIDS AND APPLIANCES RESULTING FROM SAID METHOD

(75) Inventors: Philippe Sierro, Villenave d'Ornon (FR); Didier Roux, Herignac (FR); Joël Pascal, St. Medard en Jalles (FR); Annie Colin, Bordeaux (FR)

(73) Assignee: Rheocontrol, Pessac (FR)

( * ) Notice: Subject to any disclaimer, the term of this patent is extended or adjusted under 35 U.S.C. 154(b) by 0 days.

(21) Appl. No.: 09/555,760
(22) PCT Filed: Dec. 3, 1998
(86) PCT No.: PCT/FR98/02614
§ 371 (c)(1),
(2), (4) Date: Jun. 2, 2000
(87) PCT Pub. No.: WO99/30129
PCT Pub. Date: Jun. 17, 1999

(30) Foreign Application Priority Data

Dec. 4, 1997 (FR) .............................. 97 15577

(51) Int. Cl.[7] .............................. G05D 23/00
(52) U.S. Cl. .......................... 700/281; 700/285; 73/594
(58) Field of Search .......................... 700/285, 281, 700/200, 282; 73/594

(56) References Cited

U.S. PATENT DOCUMENTS 3,667,286 A    6/1972  Kaufman et al. ............... 73/59
3,963,440 A  * 6/1976  Stein et al. .................. 204/402
4,352,287 A   10/1982  Orth et al. ...................... 73/60

(List continued on next page.)

FOREIGN PATENT DOCUMENTS

EP   0528078   2/1997   .......... G01N/15/02
FR   2737780   2/1997   .......... G01N/27/06

(List continued on next page.)

OTHER PUBLICATIONS

Soubiran et al, "Conductivity and Dielectric Measurements of a Lyotropic Lamellar Phasse under Shear Flow", Europhysics Letters, vol. 34, No. 4, pp. 243–248 (1995).

Jamal, R., "Graphical object–oriented programming with LabVIEW", Nuclear Instruments and Methods in Physics Research, A 352 (1994) pp. 438–441, North Holland.

(List continued on next page.)

*Primary Examiner*—Leo Picard
*Assistant Examiner*—Kidest Bahta
(74) *Attorney, Agent, or Firm*—Hayes Soloway P.C.

(57) ABSTRACT

A process and device for characterising complex fluids such as emulsions, gels, surfactant solutions and others and appliances resulting therefrom for characterising fluids on the basis of the process used. The process comprises simultaneously managing the device controlling the preparation process and the measuring device. The results of the measurements and the parameters controlling the preparation process are displayed on a common computer screen in real time, thereby enabling to establish a correlation between measurements, observation and control of the process. Two devices are disclosed, a first which is a single-function device for characterising complex fluids being manufactured, and a second, which is a multiple function device for use in laboratory formulation.

11 Claims, 13 Drawing Sheets

U.S. PATENT DOCUMENTS

| | | | |
|---|---|---|---|
| 4,544,489 A | | 10/1985 | Campbell et al. ........... 210/709 |
| 4,567,765 A | * | 2/1986 | Rao et al. ...................... 73/594 |
| 4,938,602 A | * | 7/1990 | May et al. ................... 356/435 |
| 5,770,795 A | | 6/1998 | Behar et al. ................ 73/54.23 |
| 6,006,831 A | * | 12/1999 | Schlemmer et al. ... 166/250.01 |
| 6,139,782 A | * | 10/2000 | Akhavan-Tafti et al. .... 252/700 |

FOREIGN PATENT DOCUMENTS

| | | | |
|---|---|---|---|
| GB | 2191280 | 12/1987 | .......... G01N/21/51 |
| JP | 60-210751 | 10/1985 | .......... G01N/27/04 |
| SU | 1719969 | 3/1992 | ........... G01N/11/00 |
| WO | WO 95/12122 | 5/1995 | .......... G01N/27/07 |

OTHER PUBLICATIONS

Panizza, P., "A dynamic study of onion phases under shear flow: size changes", Eur. Phys. J.B 4, pp. 65–74 (1998).

Link, A., "Light Scattering from Dilute Polymer Solutions in Shear Flow", Macromolecules 1993, 26, pp. 464–471.

Sierro et al, "Structure of a Lyotropic Lamellar Phase under Shear", Physical Review Letters, vol. 78 No. 8, (1997).

Gregson et al, "A Couette cell with fixed stator alignment for the measurement of flow modified permittivity and electro-viscosity" J. Phys. E. Sci. Instrum, vol. 16 (1983).

Diat et al, ""Layering" effect in a sheared lyotropic lamellar phase", Physical Review E, vol. 5, No. 4, (1995) pp. 3296–3299.

Panizza et al, "Viscoelasticity of the Onion Phase", Langmuir 1996, 12, pp. 248–252.

Roux et al, "Dynamics of lamellar phase under flow", The American Institute of Physics, 1999 pp. 93–104.

Mandrake et al, "Large–Scale Windows 95 based Data Acquisition system", Computers in Physics, Sep. 1997, pp. 498–507.

* cited by examiner

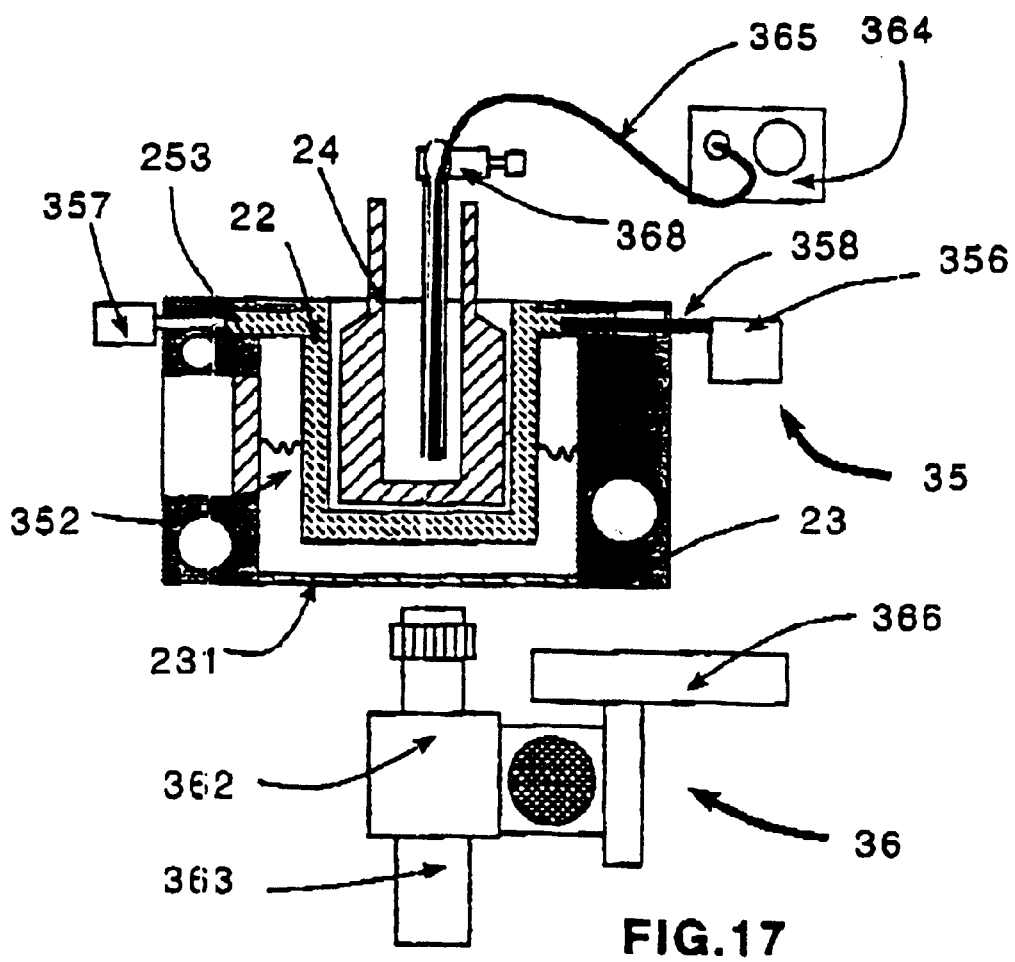
FIG.17
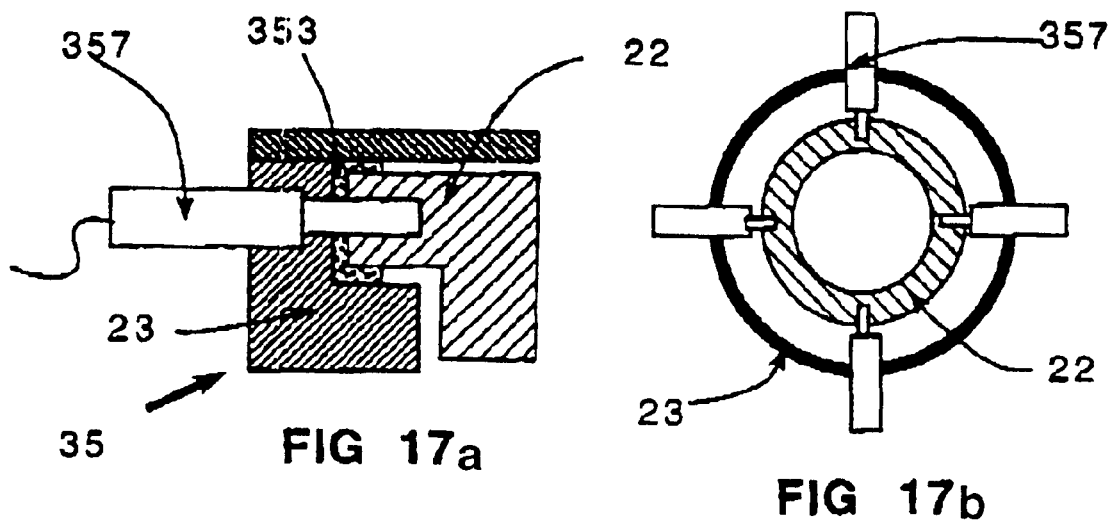
FIG 17a  FIG 17b

METHOD FOR CHARACTERIZING COMPLEX FLUIDS AND APPLIANCES RESULTING FROM SAID METHOD

FIELD OF THE INVENTION

The present invention relates to a new measurement and observation process for the characteristics of changing complex fluids from the start of their implementation to the end of their production. On the basis of these processes, certain phases of which are known, several devices, for which we will essentially give the two most interesting embodiments, will be designed.

Fluids referred to as complex such as: emulsion, gels, dilutions of different liquids, dispersions, etc. are frequently used in the agri-food industry, the beauty product industry, particularly in cosmetics, in the petroleum industry and in the chemical industry in general. The complexity of these fluids lies in the fact that their characterisation depends equally on the chemical composition, processing and preservation processes and many other parameters. In this way, the same chemical formulation does not enable:

The direct industrial reproduction of the laboratory formulation.

The industrial reproduction of identical products from different manufacturing batches.

The production of particles of a given size.

A guarantee that ageing (coalescence, decantation) will have a constant duration.

It is also very difficult to find out the emulsifying qualities of products, for example, in the case of:

An emulsifier bound to other compounds

A mixing geometry for a desired formulation.

Let us take the case of the food industry (e.g. mayonnaise). If we consider this type of emulsion, we obtain a probability of an unsatisfactory result (high failure rate), therefore unacceptable for industrial manufactures.

Let us take a second example in the case of the beauty product industry, a moisturising cream; for some batches, it is not possible to implement the manufacturing process to achieve the result, i.e. the preparation will not emulsify, resulting in unusable costly rejects.

To achieve a satisfactory result (reliability approaching 100%), it is necessary to characterise all the physical and chemical formulation parameters of the manufacturing processes. It is for this reason that the invention with measurement or monitoring devices adapted to these requirements has been proposed.

PRIOR ART

The documents of the prior art accessible to the public use known means which can improve the manufacturing processes of these complex fluids empirically. The numerous existing publications describe means which are rather measurement arrangements which improve the knowledge of complex fluids slightly without solving the formulation problems completely.

The specialist can currently use a certain number of monitoring and measurement tools; however, they do not enable him to predict the quality of the product, since this information is only fragmented and is not coordinated.

The main parameters (measurements and observations) essential for a correct complex fluid manufacturing procedure are:

1—Monitoring of the viscosity (the most frequently observed parameter)

2—Optical microscopy monitoring making it possible to identify the texture of the fluid, particularly the grain or particle size, either by sampling or in the presence of shearing forces.

3—A mean particle size measurement by diffusion of a radiation by a laboratory means (such as COUETTE cell) still, for example, under the effect of shearing, or by sampling and dilution 4—A dielectric conductivity measurement of the materials still during the formulation of the complex fluid 5—Turbidity monitoring by measuring the light intensity transmitted through the sample (case of sedimentation).

All these measurements are made with separate devices either by sampling, which disturbs the medium, or with devices with a single-function means which cannot reveal the exact state of the complex fluid.

1—Case of sampling

The disturbance of the medium induces a measurement not corresponding to the state of said medium for various reasons, difference in time, influence on medium, etc.

2—Case of a single "in situ" measurement

One measurement or observation alone be used to characterise the entire complex fluid. All the parameters obtained show a great inconsistency with no correlation.

However, we will mention three documents which approach the problem to be solved, but do not solve it completely.

The SOUBIRAN publication in EUROPHYSICS LETTERS 31-4 pages 243 to 246 in 1995 describes a dielectric conductivity measurement geometry under shearing. However, it cannot be used to obtain a result that can be used industrially, since the measurement is restrictive and the acquisition cannot be exploited directly.

The U.S. Pat. No. 4,352,287A (ORTH HEINZ W ET AL) describes a computerised device making it possible to analyse the viscosity under shearing alone, a mechanical parameter that overall is for the characterisation of a complex fluid, under shearing in a precise way; it is a specific viscometer, the principle of which differs from that of the present invention.

The document WO 95 12122 (AGRONOMIQUE INST NAT RECH) is a device which only performs a conductivity measurement during the mixing of the complex fluid, which is insufficient to find out the variation.

To characterise in-process complex fluids well, it is possible to either analyse a single physical characteristic, e.g. the electric conductivity by obtaining the highest number of measurements related to this value, exhaustively, or analyse all the significant physical characteristics so as to establish the correlations between measurements and observations, resulting in the definition of two types of devices: the first more of the single-function type well-adapted to in-process monitoring, the second of the multi-function type making it possible to obtain a better characterisation of the formulation of complex fluids.

In the case of our invention: this new process P makes it possible to characterise and measure all the accessible parameters of the complex fluid with measurement and simultaneous characterisation operations performed on the same sample by managing, at the same time, the control means in conjunction with the measurement means, thus by simultaneously displaying the data on a computer screen, storing all the data in memory to be able to retrieve it at any time.

establishing and using correlations, particularly in relation to time, with said data which directly depends on the characteristics of the complex fluids to be managed, giving significant measurements making it possible to achieve industrial manufactures. This process will then consist of comparing the analysis results obtained previously on the fluids simultaneously to the in-process results obtained, in order to deduce the correlations making it possible to predict the variation of the complex fluid manufacture. The present invention fulfils these requirements in two embodiments of devices depending on the above process, which will now be described in succession, in two non-restrictive examples of embodiments.

BRIEF DESCRIPTION OF THE DRAWINGS

The present invention will be understood more easily and its advantages illustrated more clearly upon reading the following description with reference to the accompanying figures, wherein

FIG. 17 shows the microscopic measurement, viscosity determination and lifting means;

FIG. 17A shows the details of the lifting means tank of the tank receiving the complex fluid;

FIG. 17B shows the details of the tank positioning means, i.e. a lubricated blade or a positioning cylinder system;

DESCRIPTION

Figure 1:
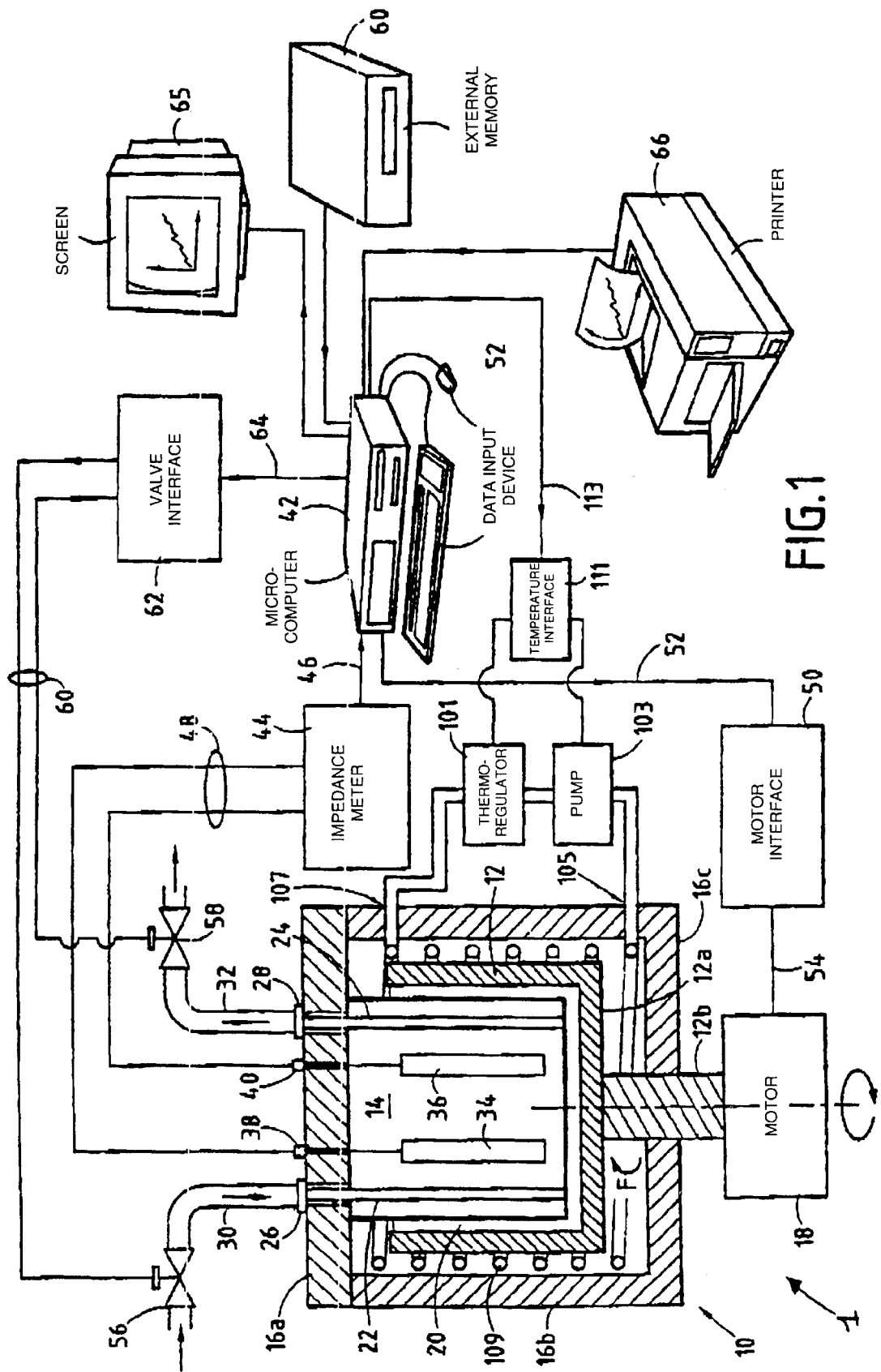
FIG. 1 is a schematic view of the automated measurement device 1 according to a first embodiment of the present invention.

In a first embodiment, the invention consists of a device which measures the conductivity, a parameter mentioned in the prior art.

The invention particularly makes it possible to monitor the variation of the fluid when said fluid is being prepared in an industrial scale formulation process wherein it is subjected to a mixing phase.

In this case, the process comprises at least one preliminary step consisting of establishing a correspondence between the flow to which the fluid is subjected during said mixing phase and the flow with shearing of the same fluid in the shearing cell. Once this correspondence has been established, it is possible to correspond the shearing rate in the cell with said mixing, in order to be able to monitor the variation of the fluid being prepared by means of the measurements made in the shearing cell. In a second variant of the process, the fluid will be injected into the measurement cell from a mixing phase in order to control said mixing phase directly.

The information collected using the shearing cell may then be used to control the mixing rate and/or time as a function of the anisotropy determined using the conductivity or impedance transition measurements.

According to a third aspect of the invention, a macroscopic property characterisation of a fluid based on the variation of said fluid's electric properties over time, following a change in the shearing rate or shearing strain, is proposed.

The inventors observed that this variation contains information making it possible to identify the fluid's dynamic phases or parameters detected at a macroscopic scale easily.

According to this aspect of the invention, the process may be detailed as follows:

subjecting the fluid to a first shearing rate or shearing strain, measuring the conductivity or impedance of this fluid in a determined direction with respect to the flow of this first shearing rate or shearing strain, subjecting the fluid to a second shearing rate or shearing strain, different to the first and measuring a modification of the conductivity or impedance of this fluid in a determined direction with respect to the flow of this first shearing rate or shearing strain, said parameter being expressed by said variation of the conductivity or impedance.

Advantageously, the variation is measured over a period making it possible to determine a stabilisation of the conductivity or impedance of the fluid, the stabilisation time expressing a modification of a fluid structural element.

The first shearing rate or shearing strain may be less than the second shearing rate or shearing strain. In this case, the stabilisation time expresses a destruction of a fluid structural element.

Conversely, the first shearing rate or shearing strain may be greater than the second shearing rate or shearing strain. In this case, the stabilisation time expresses a relaxation of a fluid structural element.

An efficient characterisation of this dynamic behaviour of the fluid may be obtained with an abrupt transition from the first shearing rate to the second shearing rate.

Naturally, it is possible to implement this third aspect of the invention by adapting the programming.

Figure 2A:
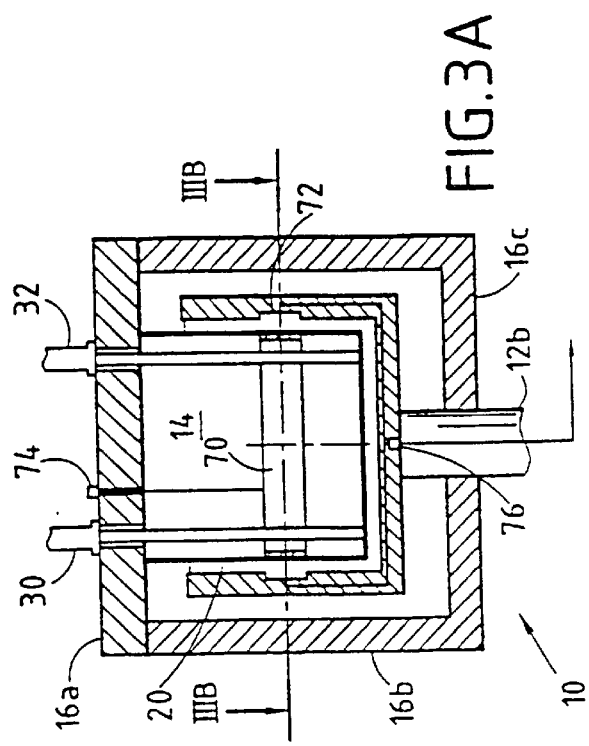
FIG. 2A is a schematic section view of a shearing flow cell enabling a measurement of the impedance or dielectric constant of a fluid in the direction of the flow velocity.
Figure 3A:
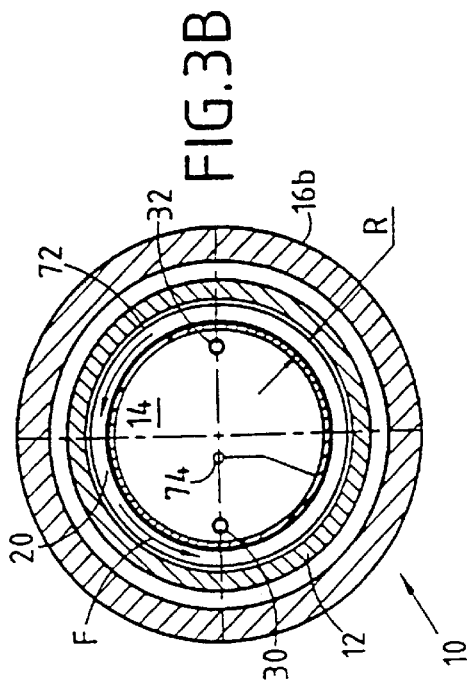
FIG. 3A is a schematic section view of a shearing flow cell enabling a measurement of the impedance or dielectric constant of a fluid in the direction of the shearing of the fluid.
Figure 2B:
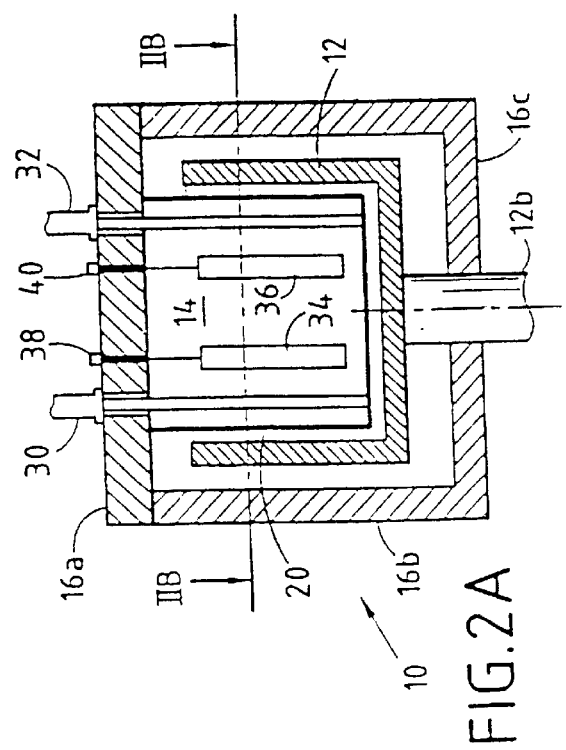
FIG. 2B is a plane schematic view of the cell in the axis IIB in FIG. 2A.
Figure 3B:
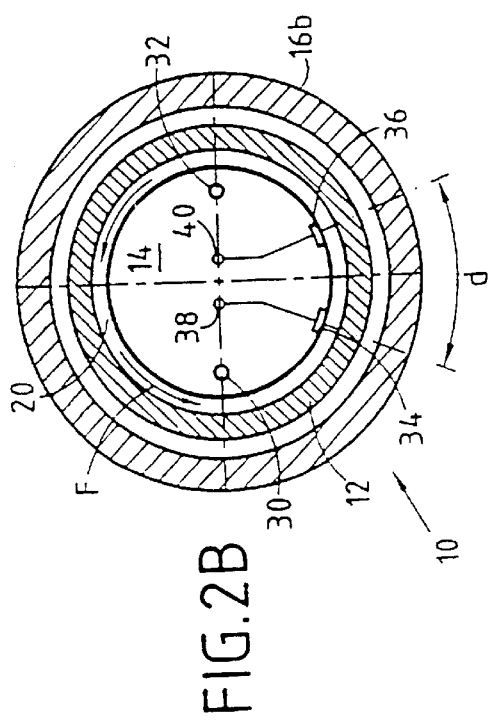
FIG. 3B is a plane schematic view of the cell in the axis IIIB in FIG. 3A.
Figure 4:
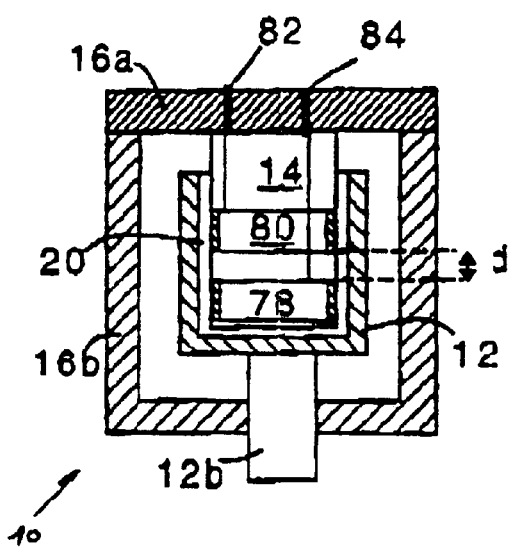
FIG. 4 is a schematic section view of a shearing flow cell enabling a measurement of the impedance or dielectric constant of a fluid in the direction of the vortex.
Figure 4A:
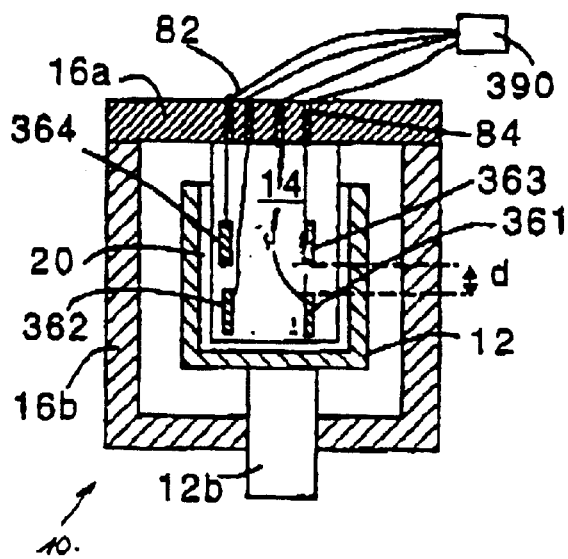
FIG. 4A is a schematic section view of a shearing flow cell enabling a measurement of the impedance or dielectric constant of a fluid in three different directions (in the direction of the flow velocity, in the direction of the vortex, in the direction of the rate gradient) in a sequential fashion.
Figure 5:
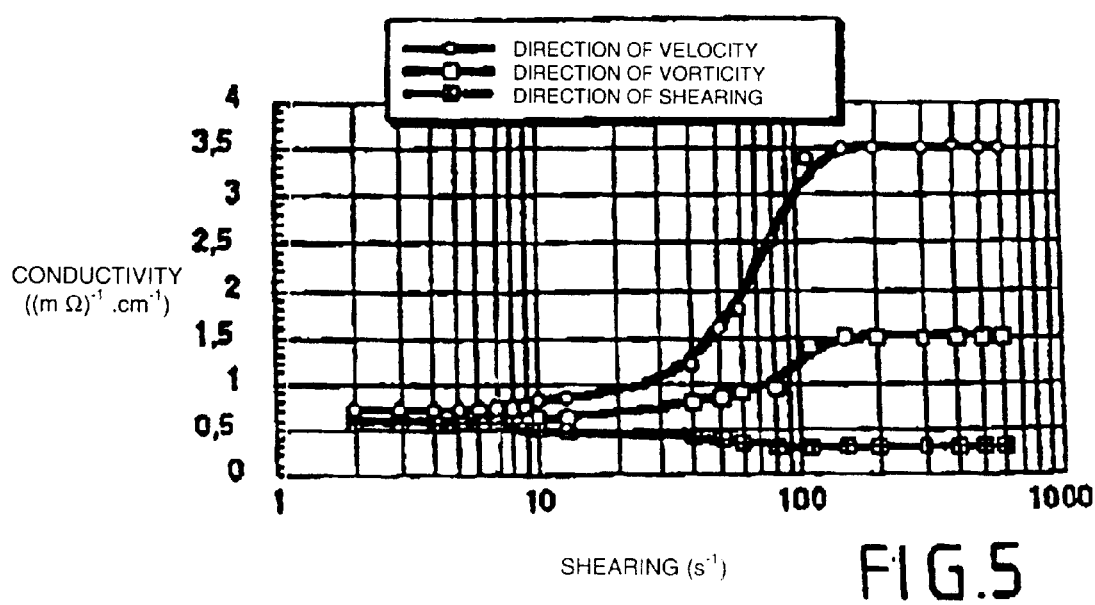
FIG. 5 is a curve showing the conductivity as a function of the shearing of a fluid subjected to an isotropic anisotropic transition, the conductivity being measured in the direction of shearing, in the direction of the fluid velocity and in the direction of the vortex.
Figure 6:
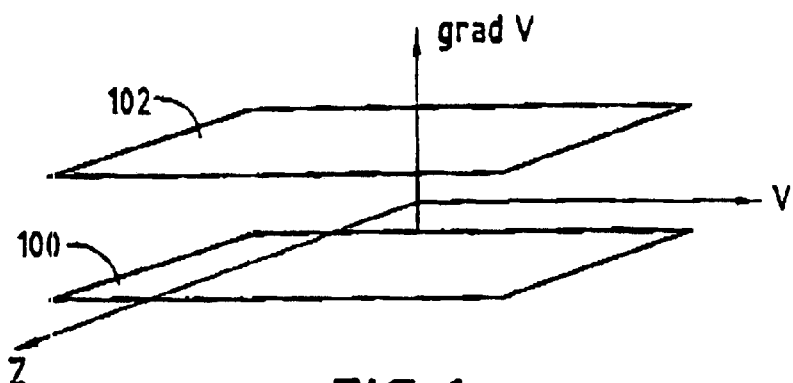
FIG. 6 is a diagram showing the orientation under shearing in a fluid with a lamellar phase.
Figure 7:
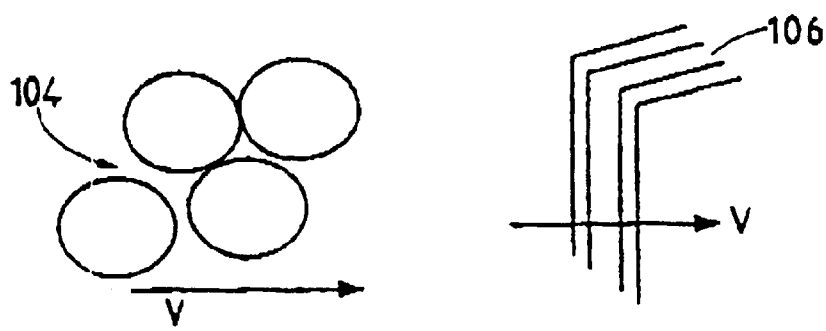
FIG. 7 is a diagram showing an isotropicanisotropic transition of the structure of a fluid under flow with shearing
Figure 8:
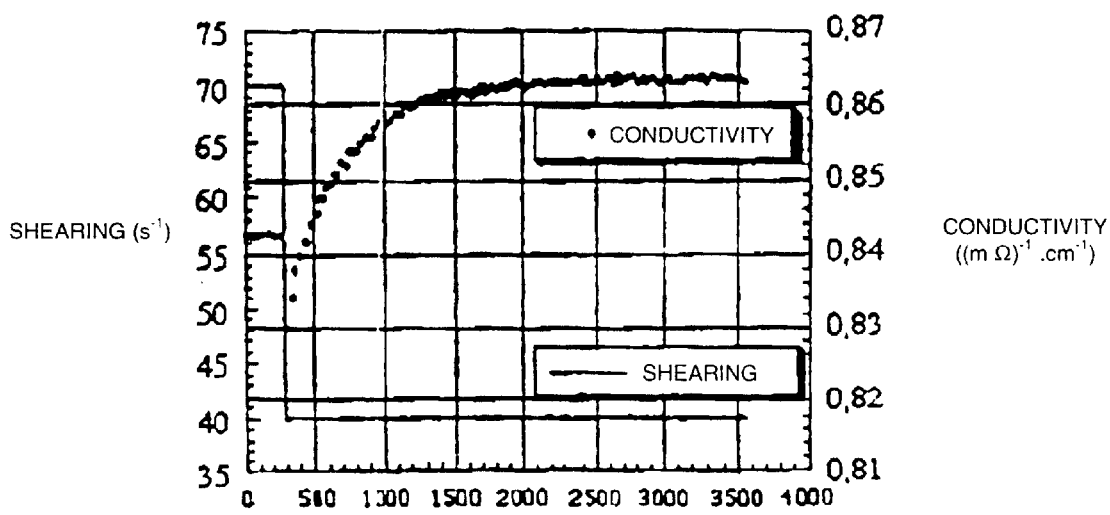
FIG. 8 is a curve showing the variation as a function of the conductivity time of a fluid in the direction of the flow rate in the event of an abrupt change of shearing rate, revealing a multi-lamellar vesicle phase.
Figure 9:
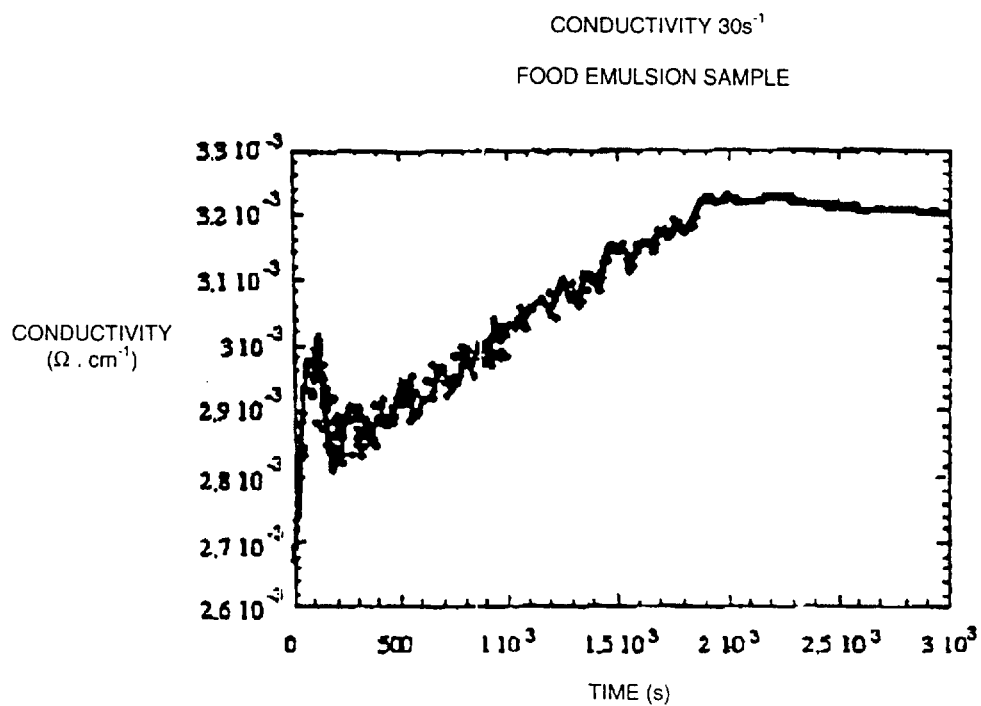
FIG. 9 is a curve showing the variation of the conductivity of a fluid in emulsion form as a function of time for a given shearing rate.
Figure 10:
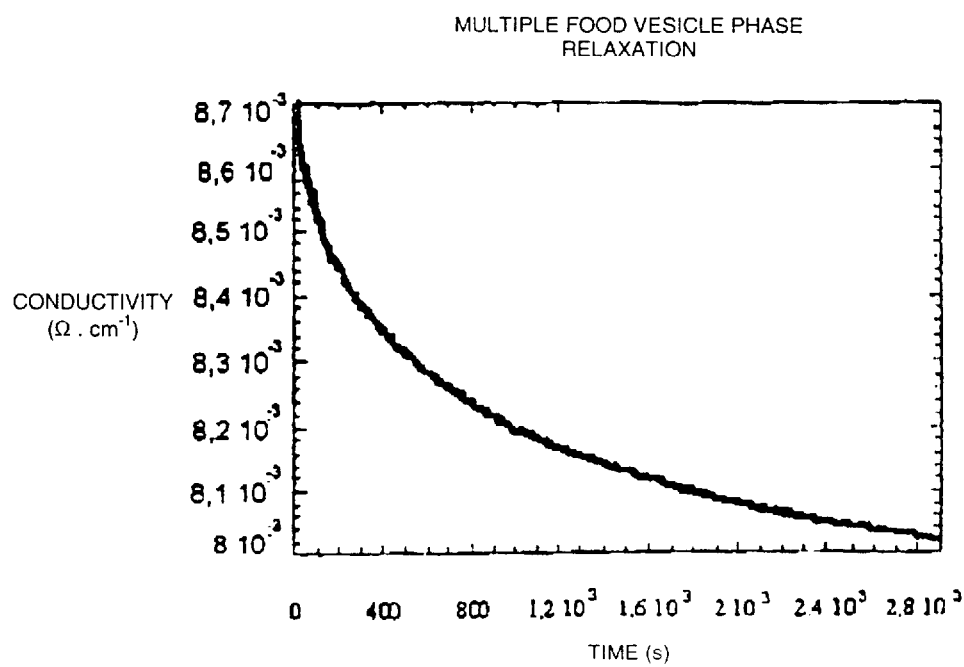
FIG. 10 is a curve of the variation of conductivity of a fluid as a function of time after shearing is stopped, reflecting the stabilisation time of a multi-lamellar phase induced by shearing.
Figure 11:
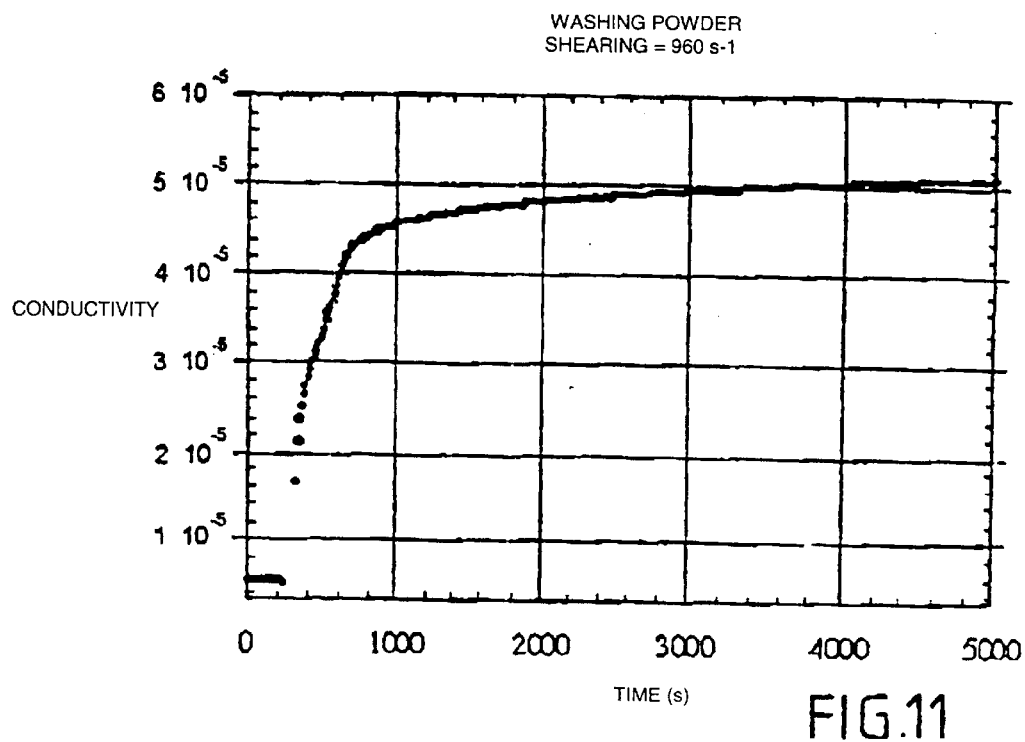
FIG. 11 is a curve of the variation as a function of time of the conductivity of a fluid containing a powder in dissolution, under a given shearing rate.
Figure 12:
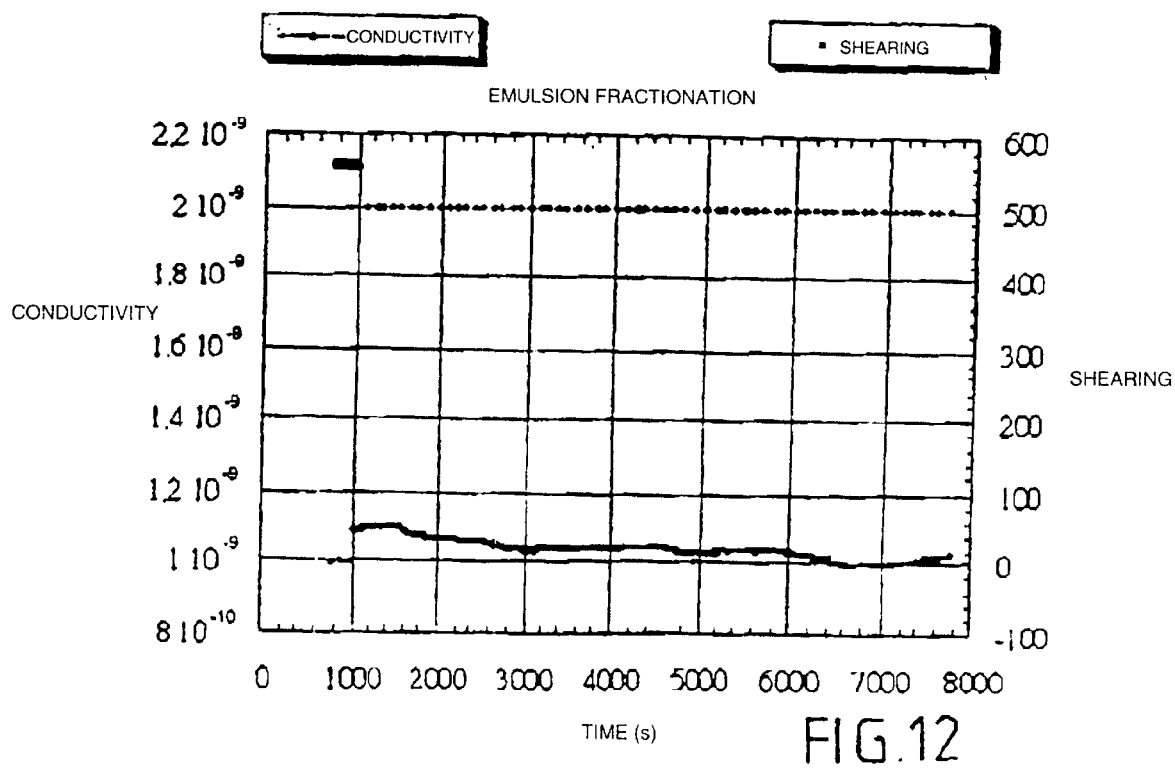
FIG. 12 is a curve of the variation of the conductivity of an emulsion as a function of time for an abrupt increase in the shearing rate.

The present invention will be understood more easily and its advantages illustrated more clearly upon reading the following description of a first embodiment, given purely as an example with reference to the accompanying FIGS., wherein FIG. 1 is a schematic view of the automated measurement device 1 according to the present invention;

FIG. 2A is a schematic section view of a shearing flow cell enabling a measurement of the impedance or dielectric constant of a fluid in the direction of the flow velocity;

FIG. 2B is a plane schematic view of the cell in the axis IIB in FIG. 2A,

FIG. 3A is a schematic section view of a shearing flow cell enabling a measurement of the impedance or dielectric constant of a fluid in the direction of the shearing of the fluid;

FIG. 3B is a plane schematic view of the cell in the axis IIIB in FIG. 3A,

FIG. 4 is a schematic section view of a shearing flow cell enabling a measurement of the impedance or dielectric constant of a fluid in the direction of the vortex;

FIG. 4A is a schematic section view of a shearing flow cell enabling a measurement of the impedance or dielectric constant of a fluid in three different directions (in the direction of the flow velocity, in the direction of the vortex, in the direction of the rate gradient) in a sequential fashion;

FIG. 5 is a curve showing the conductivity as a function of the shearing of a fluid subjected to an isotropic anisotropic transition, the conductivity being measured in the direction of shearing, in the direction of the fluid velocity and in the direction of the vortex;

FIG. 6 is a diagram showing the orientation under shearing in a fluid with a lamellar phase;

FIG. 7 is a diagram showing an isotropic-anisotropic transition of the structure of a fluid under flow with shearing;

FIG. 8 is a curve showing the variation as a function of the conductivity time of a fluid in the direction of the flow rate in the event of an abrupt change of shearing rate, revealing a multi-lamellar vesicle phase;

FIG. 9 is a curve showing the variation of the conductivity of a fluid in emulsion form as a function of time for a given shearing rate;

FIG. 10 is a curve of the variation of conductivity of a fluid as a function of time after shearing is stopped, reflecting the stabilisation time of a multi-lamellar phase induced by shearing;

FIG. 11 is a curve of the variation as a function of time of the conductivity of a fluid containing a powder in dissolution, under a given shearing rate, and FIG. 12 is a curve of the variation of the conductivity of an emulsion as a function of time for an abrupt increase in the shearing rate.

FIG. 1 is a schematic representation of an automated measurement device 1 enabling the analysis of the electrical characteristics, such as the impedance or dielectric constant, of a fluid under the effect of the flow with shearing.

The measurements are made inside a cell 10, or Couette cell, specially designed to induce, in a controlled manner, a flow state in a fluid with shearing. This cell 10, which is generally cylindrical, is represented in the FIG. as a section along its main axis.

The cell 10 is broken down into a mobile part 12, or rotor, and a fixed part 14, or stator, both integrated into a frame comprising an upper plate 16a, a cylindrical wall 16b and a base 16c.

The rotor takes the form of a cup 12 in which a central shaft 12b extends from the base 12a. This shaft 12b passes through the base 16c of the frame and is connected to a motor 18 that rotates the cup 12.

The stator takes the form of a cylindrical sleeve 14 depending on the upper plate 16a of the frame so as to be projected into the cup 12. The outer surface of the sleeve 14 and the inner surface of the cup 12 define a narrow annular area 20 (or vortex area). The fluid undergoing the measurement is held in this area in order to be subjected to a vortex induced by the rotation of the cup 12 in relation to the sleeve 14. The shearing rate of the fluid is a direct function of the rotation rate of the cup 12. It should be noted that the shearing rate may be defined either in relation to the rotation speed of the rotor 12, or as a function of the torque applied to the rotor.

According to an advantageous optional aspect of the present invention, the cell 10 is equipped with means making it possible to introduce the fluid into the vortex area 20 and to extract it from this area from the outside. In the example shown, these means are respective ducts 22, 24 for fluid introduction and extraction. Each duct 22, 24 communicates with the vortex area 20 at the lower level of the sleeve 14 and opens onto the outside of the upper plate 16a. These ducts 22, 24 may simply consist of respective holes in the sleeve 14. Connectors 26, 28 are provided on the upper plate 16a to enable connection of the ducts 22, 24 to respective outer fluid inlet and extraction ducts 30, 32. The extraction duct 32 may be connected to a suction source.

In embodiment variants, the ducts 30 and 32 may be connected to the high volume mixing system, so as to control the mixer via the results measured by the device 1. For example, if the conductivity of the fluid from the mixing stage is no longer varied, the microcomputer 42 of the device 1 stops the mixing phase.

The connectors 26, 28 may be produced so as to enable quick and automated cell connection and disconnection.

The connectors 26, 28 may be provided to seal the cell 10 automatically from the outside environment when said cell is disconnected from the device, so as to preserve the conditions initially set inside the vortex area 20.

In the example illustrated, the cell 10 is provided for electrical characteristic measurements of the fluid in the vortex area 20 and more particularly impedance measurements of the fluid in the direction of the flow velocity, i.e. in the direction of rotation of the rotor 12 (arrow F). To do this, a pair of electrodes 34, 36 is provided on the surface of the sleeve 14. Each of the electrodes 34, 36 is composed of a metal-coated strip aligned parallel to the main axis of the sleeve 14 and connected electrically to respective connectors 38, 40 on the upper plate 16*a*.

The geometry of the cell 10 at the electrodes 34 and 36 and the contact surfaces with the fluid by the sleeve 14 and the cup 12 may be understood more easily by referring to FIG. 2B, which is a section view along the axis IIB in FIG. 2A, the latter repeating the view of the cell 10 represented in FIG. 1.

It should be noted that the dimensions of the electrodes 34, 36 and their distance d around the circumference of the sleeve 14 are calibrated to enable a calculation of the impedance or conductivity of the fluid subjected to the measurement.

The device according to the invention makes it possible to control all the measurement conditions inside the cell 10 using a programmed microcomputer 42.

To this end, the microcomputer 42 is functionally connected to a digital control impedance meter 44 by means of a data bus 46. The impedance meter 44 is connected by wiring 48 to the two electrodes 34, 36 so as to be able to collect and record impedance values between these electrodes at determined intervals. The impedance meter 44 emits direct current or alternating current voltages to the electrodes 34 and 36. In the latter case, the current frequency may be programmed using the microcomputer 42 via the bus 46 over a range from a few Hz to several tens of kHz. The impedance between the electrodes 34, 36 is calculated and recorded by the microcomputer 42 for a given frequency.

The microcomputer 42 is also functionally connected to the motor 18 via an interface circuit 50 so as to control the rotation start and stop of the rotor 12, and the rotation speed or drive torque and the speed or torque variations of said rotor according to a measurement program. Conventionally, the interface 46 comprises a data input connected by a bus 52 to the microcomputer 42 so as to receive commands according to a defined protocol. These commands are converted into engagement signals which are transmitted by wiring 54 to the motor 18. For example, the motor 18 may be of the stepper motor type, in which case the interface transmits pulse and direction commands which determine the rotation speed or torque and direction, respectively.

In the example shown, the microcomputer 42 also controls the inlet and outlet of the fluid subjected to the measurement by means of a pair of electrovalves 56, 58 in the respective external ducts 30, 32. These electrovalves 56, 58 are connected by wiring 60 to an interface 62, itself connected to the microcomputer 42 by a bus 64. The opening and closing commands of the electrovalves 56, 58 are emitted on the bus 64 according to the measurement program procedure. This arrangement particularly makes it possible to load the vortex area 20 of the cell 10 with a determined quantity of fluid by actuating the electrovalve 56 of the inlet duct 30 at the beginning of measurement and then drain the area by actuating the electrovalve 58 of the outlet duct 32 and introduce a new load of fluid by actuating the electrovalve 56 of the inlet duct 30 a second time, according to a defined program. This device makes it possible to perform extraction and reinjections in a mixer and, in this case, the measurements collected are used to control the mixing application means (particularly the mixing, injection and temperature control means via the interfaces 50, 111, 62 of the device).

The connection and disconnection operations of the ducts 30, 32 may be automated by electromechanical means controlled by the microcomputer 42 in order to monitor a measurement program on several different cells in sequence. This arrangement particularly makes it possible to introduce different constituents of a fluid at determined times via respective ducts (not shown) while the cell 10 is in operation to create shearing. In this case, it is possible to provide multiple connections enabling the access of the different constituents to the cell.

In the example, the device 1 also comprises a means to monitor the temperature of the fluid inside the measurement cell 10. This means is composed of a coolant fluid (e.g. water) circulation system comprising a thermoregulator device 101 and a pump 103 connected in a closed circuit by an inlet port 105 and an outlet port 107 of the measurement cell 10 to a circulation duct 109 inside the cell. This duct takes the form of a pipe coil around the rotor (cup 12) so as to ensure satisfactory heat exchange with the fluid in the vortex area 20.

The thermoregulator and the pump 103 are controlled by the microcomputer 42 via a temperature control interface 111 and a temperature data transmission bus 113.

The thermoregulator 101 and the pump 103 may be controlled by a program to maintain a fixed temperature to set heating or cooling at a predetermined rate by means of thermostatic monitoring means known in themselves. To this end, the thermoregulator may be equipped with heating and cooling means.

This arrangement makes it possible to measure parameters of a fluid over relatively long periods, while ensuring that the temperature will remain a constant value or a controlled variable.

Other embodiments of the thermoregulator means are possible. The circulation duct may, for example, be housed in the part of the cell 10 forming the stator 14.

Similarly, it is possible to envisage a Peltier effect device housed in a part of the cell in thermal contact with the fluid to be measured, connected to a thermostatic monitoring unit, all controlled by the microcomputer 42 according to known techniques.

The measurement program may be loaded onto the microcomputer 42 from an internal memory or an external memory 60, or by a data input device 62 such as a keyboard or a mouse. The data input device 62 may particularly be used to modify the pre-recorded measurement program procedure or select parameters such as the measurement time, shearing rate (with the rotation speed) or the shearing strain rate (with the torque of the motor 18), the frequency of the current used for impedance measurements, fluid flows by the electrovalves 56, 58, etc.

According to the present invention, the microcomputer 42 is programmed to store the data measured using the cell 10 (in this case, the impedance) and correlate it with other parameters, such as the shearing rate or the shearing strain and the time elapsed from a reference point.

The microcomputer 42 produces an indication of this correlation in various forms. In the embodiment in FIG. 1, this correlation is expressed graphically on a screen 65 and on a printer output 66. Several examples of these graphic representations obtained according to the invention will be described and commented on in detail below with reference to FIGS. 5 to 11.

FIGS. 3A, 3B and 4 and 4A show variants of measurement cells 10 adapted for the measurement of the impedance of the fluid in other directions with respect to the flow. These cells are identical to that presented with reference to FIGS. 1, 2A and 2B in terms of their general design and the creation of shearing in the fluid. The common elements of all these parts are identified with the same references and therefore will not be described again in order to keep the description concise.

FIGS. 3A and 3B represent, in an axial section and plane view along the axis IIIB of said section, the cell adapted to measure the impedance between the surfaces of the rotor 12 and the stator 14 in contact with the fluid, i.e. by means of the thickness of the fluid in the vortex area 20. Therefore, this measurement expresses the impedance of the fluid in the direction of shearing or in the direction of the speed gradient Grad V.

For this purpose, the cell 10 comprises a first electrode 70 depending on the stator 14 and a second electrode 72 depending on the rotor 12. In the example, the first electrode 70 takes the form of a metal-coated ring positioned on the circumference of the stator 14. The second electrode 72 also takes the form of a metal-coated ring concentric with the first electrode. It is positioned in a groove provided on the inner surface of the cup 12 forming the rotor. The first and second electrodes 70, 72 comprise a contact area with the fluid dimensioned to enable a suitable impedance measurement.

The connection to the first electrode 70 is made using a connector 74 on the upper plate 16a of the cell, as in the example in FIG. 1. The connection to the second electrode is made using a rotary contactor 76 provided at the rotation axis, enabling a link between this electrode and a static point outside the cell 10. Such a contact technique is known in itself and may be implemented advantageously using a mercury contactor.

FIG. 4 represents an axial section of a cell adapted to measure the impedance in the direction of the main axis of the vortex area 20, i.e. in the direction of the vorticity. The electrodes take the form of two metal-coated rings 78, 80 on the circumference of the stator 14, offset from each other by a predetermined distance d to enable a suitable fluid impedance measurement.

The connection to the two electrodes 78, 80 is made by two external connectors 82, 84 on the upper plate 16a, as in the case of the cell shown in FIG. 1.

In another embodiment variant, the stator may comprise at least 4 electrodes which may be of the point type 361, 362, 363, 364, represented in FIG. 4A, arranged in an appropriate manner on the surface of the stator, connected to a rotary contactor 390 which is itself connected to an impedance meter 44 and the rotor comprises one or more annular 365 or point electrodes opposite the electrodes 361, 362, 363, 364, positioned in an appropriate manner and connected to the rotary contact 76 which is connected to the rotary contactor 390 (or sequential polarity selector, the operation of which is known) so as to measure the fluid impedance sequentially in different directions with respect to the direction of the flow rate according to the polarity of the different electrodes. This system makes it possible to characterise the anisotropy under shearing on the same sample during shearing.

The automated measurement device according to the present invention can thus make measurements with all the cells described with reference to FIGS. 2 to 4 by mere interconnection. Naturally, the device may be adapted easily to make measurements on several cells simultaneously, each cell being controlled independently in terms of shearing rate, filing and draining of the vortex area and data input.

For example, the automated measurement device according to the present invention can control the three types of cells described with reference to FIGS. 2 to 4 in order to measure the impedance of a fluid in the three directions, in the direction of the rate, shearing and vorticity, respectively. In such a configuration, it is possible to control the cells in phase and under the same shearing and data acquisition conditions to enable a variable comparison of the parameters over time. The device can thus plot the appearance or a variation of an anisotropy in the conductivity measured in two or three different directions by reproducing a curve such as that represented in FIG. 7.

In the example shown, the device is planned to determine the fluid impedance. It is clear that, using this parameter, it is possible to also determine the conductivity or dielectric constant of the fluid on the basis of fundamental correspondences.

It should be noted that the automated measurement device can also operate with other types of shearing cells to analyse various other parameters, such as the response of a fluid to radiation (optical, X photons, neutrons) and to elastic waves (acoustic, ultrasound, infrasound), etc.

Due to the measurement automation enabled by the device according to the present invention, it is possible to monitor the variation of a fluid at various stages of its formulation continuously. For example, the device may be implemented in an industrial production site of a complex fluid (cream, food composition, detergent, etc.) where mixing of the constituents is performed in a tank or similar device. The shearing cells may be connected on their inlet and evacuation ducts 30, 32 to the tank feed and evacuation system, respectively, and programmed to produce a shearing rate corresponding to that created by the mixing. The information collected on the modification of the parameters (e.g. impedance anisotropy, variation or stabilisation of impedance in the selected direction) may then make it possible to adjust the mixing conditions so as to ensure an optimisation of this operation in terms of duration, speed, etc.

The microcomputer 42 can also calculate properties of the fluid using the measurement data collected and its modification as a function of a shearing rate and/or the time elapsed. Using these properties, the microcomputer can control the procedure of a manufacturing process, e.g. in order to adhere to the specifications, via control outputs (not shown).

We will now describe using examples how it is possible to obtain electrical characteristic measurements of various fluids and information which may be deduced at a macroscopic level. Important information on the macroscopic properties is obtained by studying the anisotropy of the electrical characteristics of a flowing fluid with shearing.

For complex materials (materials with a large microscopic structure in terms of average molecule size), the dielectric measurement is a very precise probe very sensitive to the microstructure (the macroscopic conductivity is sensitive to the porosity and microscopic tortuousness of the material). An overall change in the microstructure produces an effect on the macroscopic conductivity of the material. The dielectric measurement as a function of time of a material under flow makes it possible to measure the variation time of the internal structure of the material to obtain its stationary state (flow state where the microstructure no longer varies over time). This variation time is then noted as a function of the shearing rate (or the variation in the shearing rate or shearing strain) produced. It makes it possible to optimise or monitor the manufacture according to the shearing rate produced.

If the sample is already mixed in the measurement cell, the dielectric measurement will reveal the internal structural modification at a constant concentration of the different constituents of the fluid. The variation time to achieve the stationary state is the time required by the sample from the change in flow state to the achievement of a conductivity or dielectric constant that no longer varies over time (conductivity plateau).

According to the present invention, it is also possible to mix the different constituents of the material in the measurement cell.

This operation is possible since the measurement cell according to the present invention may, in a preferred embodiment, comprise means making it possible to introduce materials into the vortex area while the cell is activated.

If the mixture consists of dispersing non-soluble particles in a fluid under flow, the variation time to achieve the stationary state is the time characterising the particle dispersion time.

If the mixture consists of dissolving soluble particles in a fluid under flow, the variation time to achieve the stationary state is the time characterising the particle dissolution time.

If the mixture consists of producing a new structure (a new material) with different fluid or solid constituents (e.g. mayonnaise), the variation time to achieve the stationary state is the time characterising the time to generate this structure.

The conductivity is measured as a function of time with, as the origin time, the fluid's change in flow state if it is already constituted, or otherwise the start of the mixture of the different constituents of the fluid.

In an industrial application, the measurement of the variation of the conductivity over time may be used as a quality control process.

Indeed, industrial manufacturers working with complex fluids (cosmetics, paints, bitumens, pastes, agri-food, petrochemicals, pharmaceuticals) encounter numerous production quality control problems.

In addition, progress in new material formulation control involves the industrial manufacturing process and product quality control. Complex fluids are produced from a mixture of formulas comprising a wide variety of different compounds.

Production includes an essential mixing phase, the purpose of which is either to form the structure (e.g. mayonnaise) or disperse one medium in another. This mixing may be carried out with very varied devices. One the parameters that remains relevant for mixers is the mean shearing rate they apply to the fluid.

In the fluid transport and pumping, the flows may induce detrimental instabilities which may result in the separation of the mixture, modifications in the viscosity or particle sedimentation. The knowledge of these structural variations makes it possible to solve these problems.

In terms of quality, the structure of the materials remains important. The smooth texture and taste of a mayonnaise, for example, depend on the size of the microscopic drops forming it. The size of these drops depends on the shearing rate during the mixture. The dissolution time of a washing powder in a machine depends on the shearing rate applied to it. The dielectric measurement as a function of time and the shearing rate make it possible to improve the quality of industrial products.

The invention makes it possible to obtain simple, reproducible measurements, characterising a phenomenon taking place at a microscopic scale for fluids with a viscosity similar to that of water and, therefore, inaccessible with rheological measurements. This technique has proved to be very accurate, for example, for the measurement of the dissolution time as a function of the shearing rate of powders in a solvent (e.g. washing powder in water).

This measurement may easily be transposed to industry since its implementation does not require advanced scientific knowledge. Once the measurements have been made on the shearing cell, it is easy to position the electrodes on an industrial manufacturing line and monitor the state of the production directly.

Due to the material transformation time measurement possibilities and the structural characterisation possibilities, the present invention is likely to favour research on new materials and reduce the manufacturing cost for numerous industrial products.

Therefore, this measurement means can make it possible, firstly, to accelerate the progress of research and, secondly, increase the competitiveness of businesses considerably.

For a material with an isotropic microscopic structure, the material's conductivity does not depend on the direction of the lines in the electric field applied during the measurement. An anisotropic material shows conductivities which depend on the orientation of the field lines. The present invention offers the possibility of measuring the conductivity of the sample in the three characteristic directions of a flow with shearing, i.e.:

the direction perpendicular to the shearing rate,
the direction parallel to the shearing rate,
the direction of the vorticity (for Couette flows).

For each direction of the flow, the conductivity of the sample as a function of the shearing rate is measured.

The anisotropy measurement of the conductivity under flow makes it possible to measure the anisotropy of materials liable to distributed by an application generating flows and shearing.

For example, the application of paint on walls using paintbrushes generates shearing liable to generate an anisotropy of the structure of the paint on the wall. Knowing this anisotropy may make it possible to solve paint spreading problems and ensure optimal conditions for the application of said paint. The same problems are found for applications of varnish, glue on adhesive tapes, etc.

An example of an anisotropy measurement of a fluid under flow with shearing will be given with reference to FIGS. 5 to 7.

FIG. 5 represents the conductivity measurement for a surfactant phase in solution (lyotropic lamellar phase) as a function of the shearing rate and for the three main directions of the flow, the direction of the flow and the two directions perpendicular to it. These directions are noted as V for the direction of the flow, Z and grad V for the other two.

In a shearing effect, shearing surfaces 100, 102 which are approximately parallel in the plane of the direction V of the flow are created in the fluid.

This curve shows that the modification in the three-dimensional conductivity of the phase depends on the shearing rate. An anisotropy that is amplified with the shearing rate is clearly observed. The conductivity in the flow direction becomes very high with the increase in the shearing rate while the conductivity in the direction grad V decreases.

This effect of the conductivity as a function of the shearing rate corresponds to a modification in the microstructure of the material. As shown in FIG. 7, said material is in the form of vesicle (isotropes) 104 for a low shearing rate and in the form of an oriented lamellar phase structure (anisotrope) 106 for a high shearing rate.

This example is characteristic of the orientation of the anisotropic materials by the shearing effect. In this case, the anisotropy is characterised perfectly by the measurement of the conductivity.

We will now describe the measurement process to determine the structural variation time of a material under flow with shearing.

The curve in FIG. 8 represents the measurement of the conductivity for a multi-lamellar vesicle phase (particles similar to liposomes) as a function of time and in the direction of the velocity. These vesicles are industrial microencapsulation products and the formation or size modification time of these microcapsules depends on the shearing rate applied. This curve shows that when the shearing rate is modified, the conductivity changes to a new stationary state. This stationary state characterises a new microcapsule size.

As shown in this curve, this technique, according to the present invention, makes it possible to measure the transition time of the material from a stationary state to another easily.

The variation over time of the electrical characteristics of a fluid under flow with shearing at a constant rate also makes it possible to obtain indications on the macroscopic properties.

For example, the curve in FIG. 9 shows the destabilisation time of an emulsion for a food product (salad dressing) for a given shearing rate. The conductivity increases to a certain level characterising the destabilisation time.

This specific example shows the potential benefits of the invention for the agri-food sector since it makes it possible to measure formation times, or destruction times in this case, of structures under flow.

The curve shown in FIG. 10 is an example of the characterisation of a material produced by research which shows restructuring after the flow has been stopped.

Using this curve, the time required by a multi-lamellar vesicle phase (liposomes) generated by shearing to stabilise after said shearing has stopped is determined.

This specific example shows a measurement of the characteristic relaxation time of a material after the end of shearing.

The curve shown in FIG. 11 shows the time required by a washing powder to dissolve in pure water at a shearing rate of 960 s−1. The sample is introduced by injection. The conductivity increases to reach a plateau characterising the total dissolution of the powder.

An example of the characterisation of the modification in the size of an emulsion under the effect of shearing is shown by the curve in FIG. 12.

The curve shows an immediate drop in the conductivity of an oil in water emulsion when the shearing changes from 0 s−1 to 500 s−1. This drop in conductivity corresponds to a significant variation in the average size of the oil drops in the emulsion.

Figure 13:
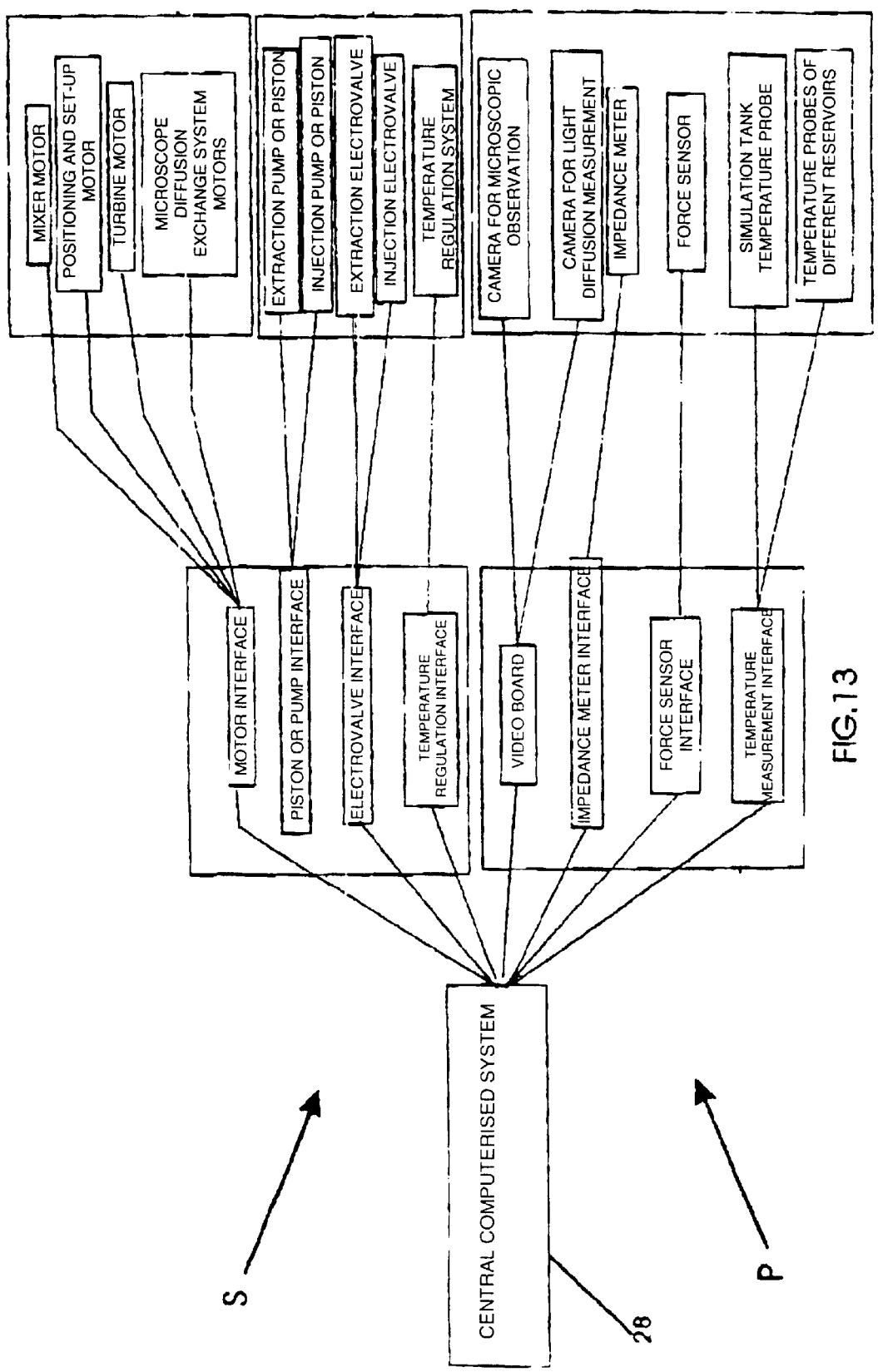
FIG. 13 shows a block diagram of a second embodiment of the invention of all the means implemented in the process P.

In a second embodiment, we will describe a multi-function device 2 capable of controlling and measuring the characteristics of a complex fluid simultaneously during its manufacturing process;

FIG. 13 shows a block diagram of all the means implemented in the process P

Figure 14:
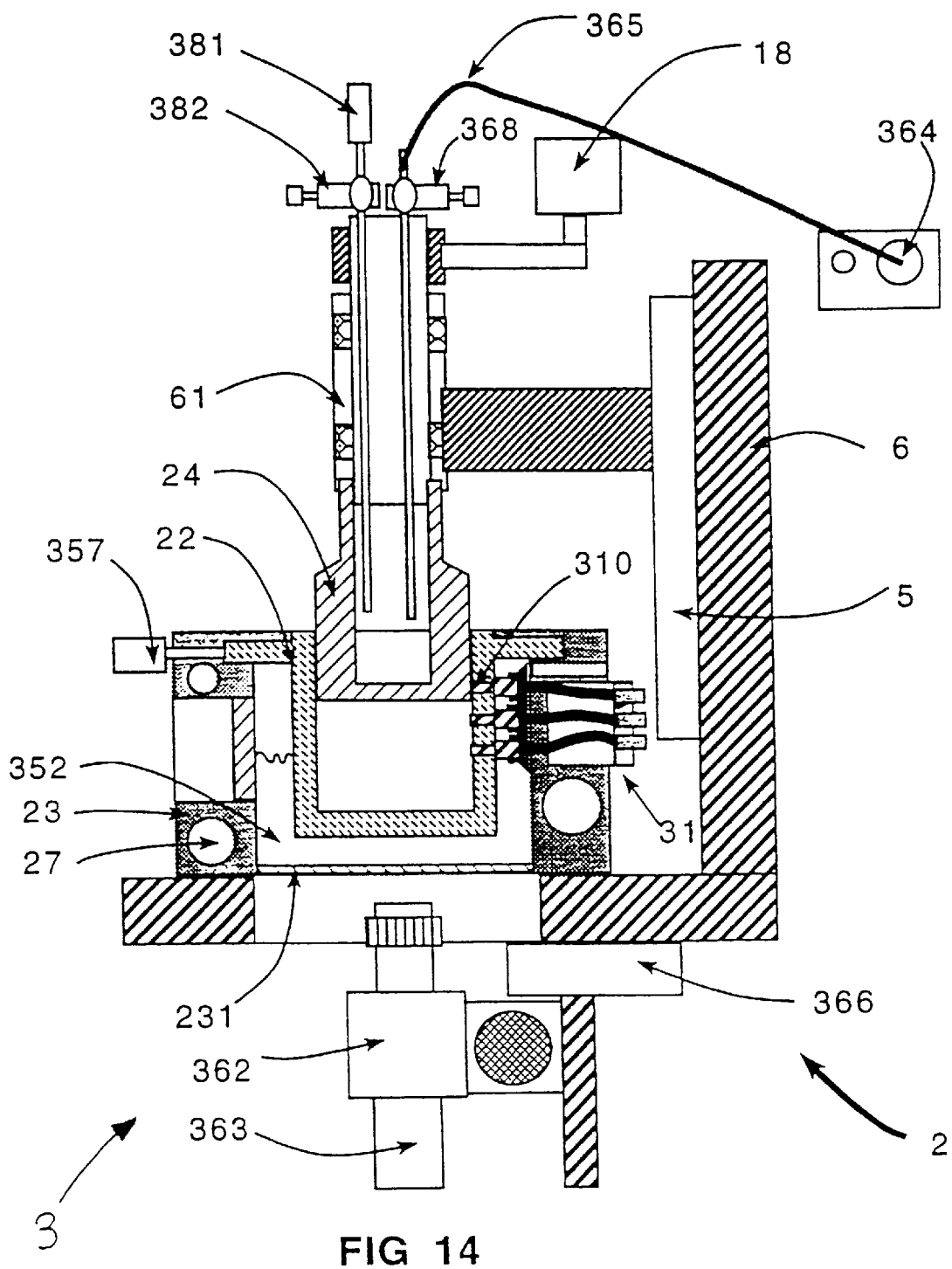
FIG. 14 shows a section view of the multi-function device 2.

FIG. 14 shows a section view of the multi-function device 2.

Figure 15:
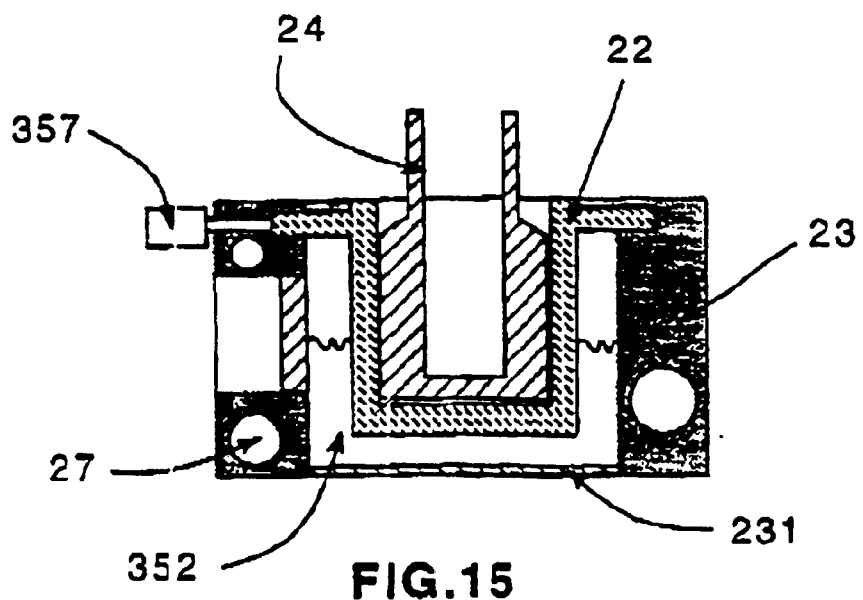
FIG. 15 shows the means implemented generating the process P (case of a "Couette" cell) to generate shearing strains and some monitoring means.

FIG. 15 shows the means implemented generating the process P (case of a "Couette" cell) to generate shearing strains and some monitoring means.

Figure 16:
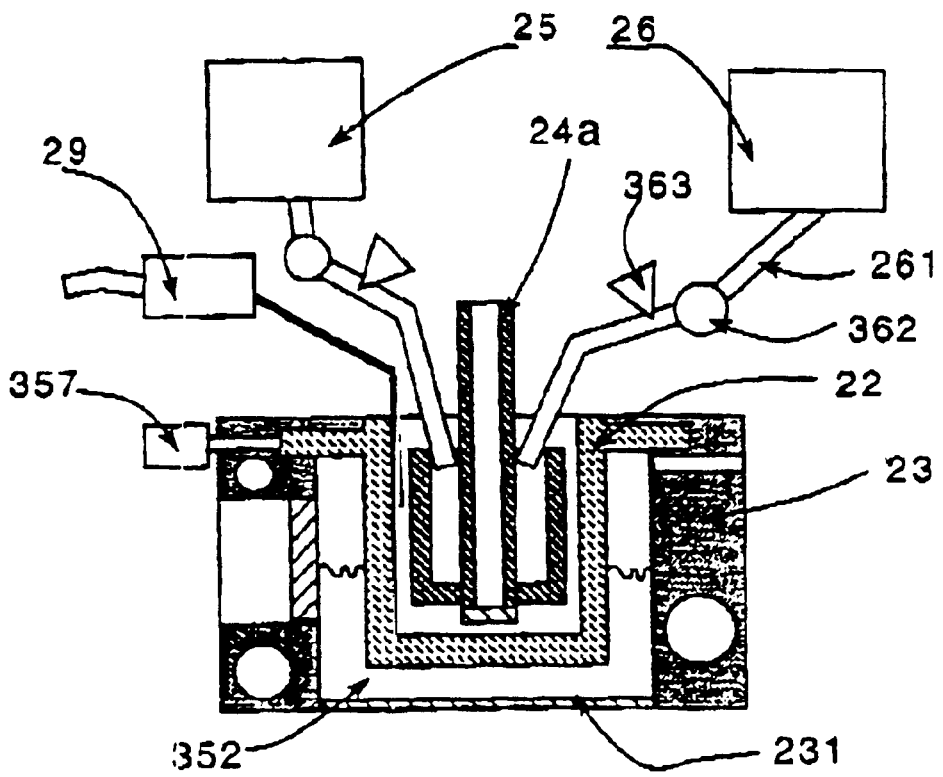
FIG. 16 shows the means implemented to generate the process (blade intended for mixing and injection and extraction system)

FIG. 16 shows the means implemented to generate the process (blade intended for mixing and injection and extraction system).

FIG. 17 shows the microscopic measurement, viscosity determination and lifting means.

FIG. 17a shows the details of the lifting means tank of the tank receiving the complex fluid.

FIG. 17b shows the details of the tank; positioning means, i.e. a lubricated blade or a positioning cylinder system.

Figure 18:
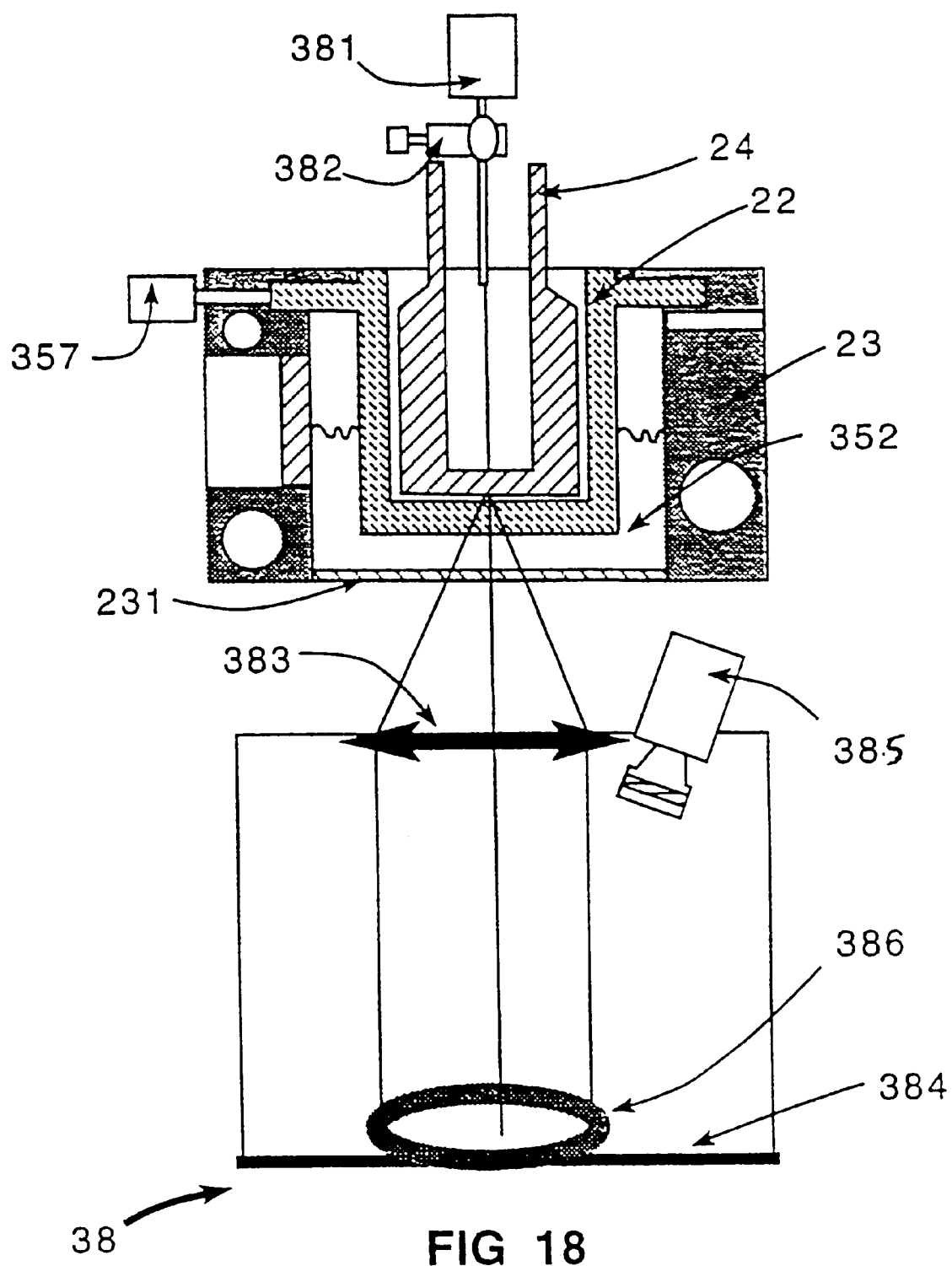
FIG. 18 shows the measurement and observation means with the emission of a laser beam through the base of the cell.

FIG. 18 shows the measurement and observation means with the emission of a laser beam through the base of the cell.

Figure 19:
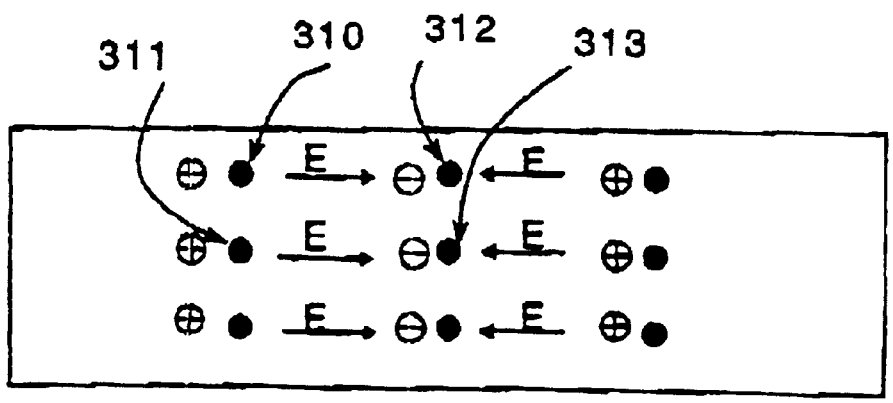
FIGS. 19 and 19A show a plane projection of the lateral surface of the cylinder showing the position of the electrodes and the orientation of the average electrical fields as a function of the polarity of the electrodes, with the stator being the tank in this case.
Figure 19A:
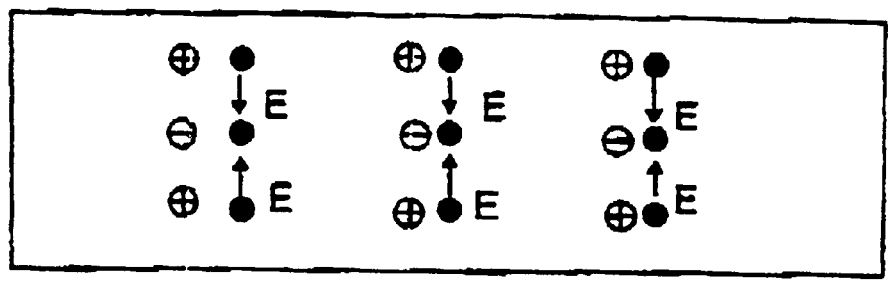

FIGS. 19 and 19a show a plane projection of the lateral surface of the cylinder showing the position of the electrodes and the orientation of the average electrical fields as a function of the polarity of the electrodes, with the stator being the tank in this case.

Figure 19B:
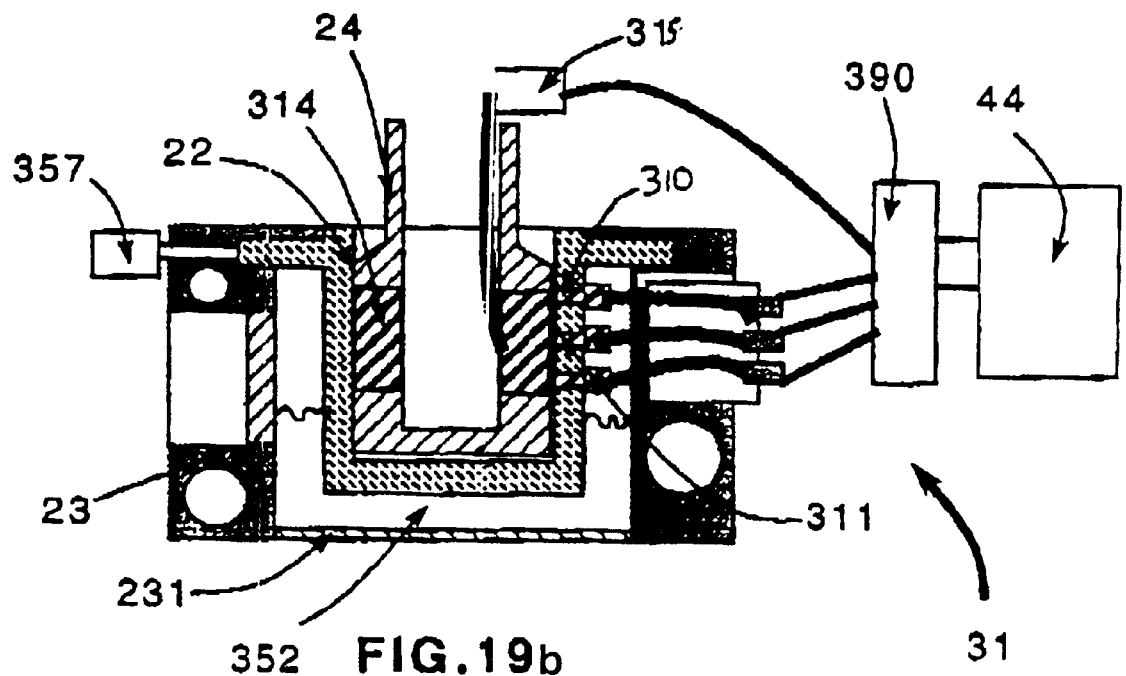
FIG. 19B shows the conductivity measurement means (couette cell section view)

FIG. 19b shows the conductivity measurement means (couette cell section view).

Figure 20:
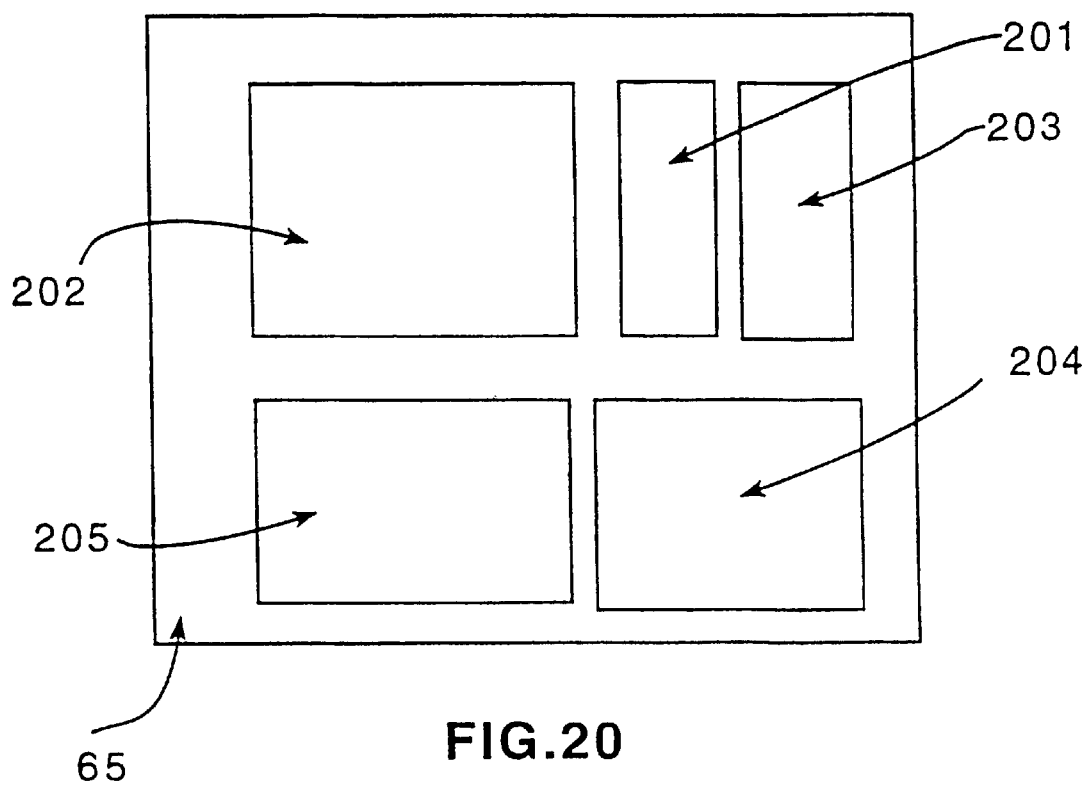
FIG. 20 shows a display of the measurements and observations on a central computerised system screen managing the entire manufacturing process of the complex fluid, the instantaneous measurements and observations and the historic curves simultaneously.

FIG. 20 shows a display of the measurements and observations on a central computerised system screen managing the entire manufacturing process of the complex fluid, the instantaneous measurements and observations and the historic curves simultaneously.

In this second embodiment (device 2), all the functions:
Rotation and control of the motor 18 corresponding to the device 1
Temperature monitoring
Shearing rate monitoring
Control of electrovalves and their function
Control of interfaces
Injection and extraction of fluids and their constituents
are managed by the same means as in the version of the device 1 or by identical means, which are therefore not described a second time in this new version of the device 2 which, unlike the first version specifies that the stator is the recipient of the complex fluid, while in the first version, device 1, the rotor was the recipient. Apart from these essential remarks for the understanding of the invention, the new means included in this new version will be described and render the invention more adapted to formulation.

The benefits of the electric. conductivity measurements and the analysis of the variations of this measurement to characterise a complex fluid have led to the development of means initially provided to obtain a better understanding of atypical variations (noise, sudden variations of parameters, direction of variation of said parameters within the fluid, etc.) and thus make a distinction between artefacts and significant signals, rendering said signals directly usable to characterise the state of the product and improve the management of the industrial process.

These means were developed in several complementary ways making it possible to distinguish between artifacts and significant value measurements, particularly by:
Simultaneously observing the electric conductivity measurement variations in the 3 axes at several levels in the tank.
Simulating experimental conditions as close to the industrial process as possible.
Attempting to establish correlations between measurements and observations.

The complex fluid is monitored in its variation, from the start of its use (or before the mixture and from the addition of all the products, both solid and liquid) to the end of its manufacture.

This set of various products is therefore placed in a recipient tank 22, which may be directly the stator of the device or the Couette cell in the second embodiment (Device 2).

A rotor 24 or a blade 24a is lowered into the tank 2 (FIGS. 14 and 16) by a positioning means 5 controlled by a computer system 28 in direct application on the constituents of the complex fluid; the multi-function device is thus loaded.

Following this loading, the process may be started according to the operations managed simultaneously by the system 28 controlling said process Variation of the rotation speed of the rotor 24

Injections of the liquids or gases placed in two reservoirs 25 and 26

Temperature rise of device 2 by circulating water in a toric chamber 27 or by a system similar to a radiator Possible variation of this temperature Recovery of the complex fluid by extraction systems, e.g. pumps 29.

The multi-function device 2 is attached onto a frame 6; it also comprises measurement and observation means 3 composed of:

A shearing conductivity measurement system 31 (FIG. 19), said system 31 comprises at least four point electrodes 310, 311, 312, 313, for example, level with the inner surface of the tank 22 or which may be fitted directly on the base of said tank and on the rotor; These electrodes are connected to a rotary connector system 390 which changes the polarities of the electrodes connected to an impedance meter 44 (managed by 28) sequentially so that the dielectric conductivity measurement is made in the direction of the electric field E, in the different directions of the flow, FIG. 19 and 19a, the annular electrodes 314 of the rotor being connected to rotary contacts 315; this sequential measurement makes it possible to measure the anisotropy of the samples of complex fluids under shearing in a single experiment.

A viscosity measurement device 35 comprising, for example, lifting means 352 contained in the chamber 23 which may be a suitable liquid (applying buoyancy) and a lubricated blade device 353 which enables the rotation of the tank using the viscosity force of the sample placed in the tank.

After a micro-rotation of the tank 22 with reference to the chamber 23, a sensor 356 (movement, force or torque measurement sensor, etc.) connected to 28 makes it possible to measure the resulting viscous force applied to the sample placed in said tank, in contact with the rotor, using a rod 358 attached to the tank.

The viscosity measurement device 35 comprises at least three cylinders 357 controlled by the computerised system 28 making it possible to reposition the tank using a lubricant such as a viscous paste.

Microscopic observation means 36 comprising a microscope 362 equipped with a camera 363 still controlled or managed by 28, comprising a movement means 366 to explore the transparent base of the 22 via the transparent base 231 of the chamber 23. The base of 22 may have a flat or conical shape, the lighting of the observation system is composed of a light source 364 comprising a positioning system 368 in which the light follows an optical fibre 365 routed through the hollow shaft of the rotor 24 or the blade 24a to the transparent base of the tank 22. The conical shape of the base of the rotor 24 in contact with the sample makes it possible to select the thickness of the sample and thus analyse, even in the event of high diffusion (high turbidity).

In an embodiment variant of the device 36, the rotor 24 or 24a comprises a reflective base; the light in contact with the sample follows the optical fibre 365 and, in this case, lights the rotor 24 or the blade 24a from underneath the tank 22 with the transparent base 231 of the chamber 23.

A set of light diffusion means composed of:

A laser source 381, the beam of which passes through the base of the rotor 24

An optical collimation system 383

A luminescent screen 384

A camera 385 filming the optical diffusion spectrum 386 on the screen 384.

It is important to note that for mixing with rotary blades 24a, the microscopic observation and diffusion measurements are carried out according to the following process:

The blade stops turning and an automatic positioning system 5 lowers the blade to obtain the light diffusion measurement or microscopic observation, for a very fine sample thickness (approximately 10 microns). After this observation, the system is repositioned and resumes its initial rotation.

As shown in the display S of the process P in FIG. 13, the multi-function device 2 is controlled and managed in terms of measurement acquisition by a specific computer program operating with the computerised system 28 (management and acquisition application) which makes it possible to operate the multi-functions of the device 2 automatically or manually.

In this way, different windows may be displayed simultaneously on a screen 65 (FIG. 20):

a window for all the measurements 201 a window for the historic result curves 202 a window for the control parameters 203 windows for each microscopic and light diffusion observation 204

The program can also be used to access several operating modes and the operator can:

either program various processes and measurement acquisition frequencies inherent to the complex fluids observed himself or run a process auto-control program according to the complex fluid to be studied or manufactured.

All these functional possibilities enable a specialist user to characterise the complex fluids observed, with maximum efficiency. With this process and particularly using the multi-function device 2 resulting from the process described P, the user can also demonstrate and establish correlations between:

Firstly: the electrical measurements the grain size measurements the viscosity measurements the electric conductivity measurements and, secondly, the homogeneity of the medium, its texture, stability, emulsifying power and the efficiency of the different complex fluid mixing arrangements. Said multi-function device 2 thus makes it possible to characterise a complex fluid from start to finish, in order to control an industrial manufacturing process of a very large number of fluids.

In addition to all the functions already described through the physical, mechanical and computer provided, it is possible to mention other advantages, such as:

the ability to characterise fluids in a very comprehensive manner the ability to perform operations in a very short experimentation time, with very easy interpretation of all the results obtained the device is formed of different assembled modules, which can therefore be disassembled, enabling cleaning and aseptic treatment, if required.

Finally, we would like to underline the fact that the two devices described are complementary, the first serving essentially in manufacturing workshops, and the second being more intended for laboratories since it makes it possible to characterise complex fluids before their industrial manufactures, particularly their emulsifying properties, which will then make it possible to optimise these processes and predict the subsequent behaviour of the products in their metastable state.

Other embodiments are possible, but they will be claimed particularly if they use the same means or equivalent means to fulfil similar or identical functions. In particular, these embodiments may use different shearing arrangements: plane on plane, cone on plane, or in ellipsoid shapes, for example, in order to adapt them to more specific fluids.

What is claimed is:

1. A process for characterizing complex fluids wherein the fluids include electrically conductive materials and are subjected to controlled shearing in a rheological cell or turbulent shearing in a mixing cell, according to various experimental protocols varying shearing rate, temperature, injections of constituents, and observing or measuring, according to a variation of the following parameters:

microscopic structure;

viscosity;

grain size; and dielectric conductivities or constants, in various directions and at various points, wherein said measurements and observations are performed simultaneously on the same sample and displayed simultaneously on the same screen, with microscopic observation of a physical phenomena selected from the group consisting of emulsification, coalescence, dilution, flocculation and decantation, whereby to establish correlations between:

(a) a variation of viscosity, particle size, homogeneity and texture characteristics, and (b) conductivity or resistivity measurements characteristic of said variations.

2. An automated device for carrying out the process of claim 1, comprising, in combination:

a Couette, Mooney or Cone-plane type analytical cell having a controlled shearing means;

a shearing microscopic observation means comprising:
  a microscope with a focusing system,
  a lighting system for the microscope, and
  a digital camera and associated image acquisition and processing electronics;

a light diffusion and/or turbidity monitoring system comprising:
  a laser source,
  a luminescent screen system and an optical system for obtaining a significant diffusion spectrum of particle size, and
  a digital camera and associated image acquisition and processing electronics;

a movement and to-and-fro system for horizontal adjustment and successive microscopic observations followed by light diffusion;

an automatic raising and lowering system for moving the rotor closer to the stator;

a temperature monitor and regulator;

a viscosity measurer;

a conductivity or dielectric constant measurer, comprising:
  a plurality of pairs of electrodes level with the inner surface of the analytical cell,
  a plurality of impedance monitors; and
  a computer for controlling said means and for performing, simultaneously, in real time, on the same sample:

(a) microscopic observations and size or turbidity measurements by light diffusion equally on translucent diffusing or turbid products, the rotor being conical and the microscope and the diffusion device moving horizontally in order to select a suitable thickness for a satisfactory observation, (b) viscosity variation measurements, and (c) mean conductivity or resistivity variation measurements in two directions with respect to the shearing direction, said computer having logic for managing said means simultaneously and display in several windows of the screen:

physical parameters and their variation during the experiment in the form of curves;

static or dynamic microscopic observation and light diffusion windows; and instantaneous values of said measurements and historic curves for the entire experiment.

3. An automated device according to claim 2, and including, in combination:

a tank;

a mixing blade;

a fluid or gas injector or extractor;

said device further comprising a plurality of probes for positioning at varying positions in the tank, said probes comprising electrodes impedance measuring said probes being controlled by and the results being acquired, stored and displayed by said computer, wherein said means are combined and managed by application of the same functions whereby the device measures mean conductivity or dielectric constant at several points or levels of the tank, thus permitting the establishment of correlations between variation of physical parameters, observation of macroscopic phenomena and significant measurements.

4. An automated device according to claim 2, wherein said electrodes are connected to a rotary connector for permitting adjustment of polarity on said electrodes.

5. An automated device according to claim 2, wherein said lighting system comprises a direct lighting system through the rotor shaft.

6. An automated device according to claim 2, wherein said lighting system comprises an episcopic lighting system, with the rotor being reflective.

7. An automated device for carrying out a process for characterizing complex fluids wherein the fluids are subjected to controlled shearing in a rheological cell or turbulent shearing in a mixing cell, according to various experimental protocols varying shearing rate, temperature, injections of constituents, and observing or measuring, according to a variation of the following parameters:

microscopic structure;

viscosity;

grain size; and dielectric conductivities or constants, in various directions and at various points, wherein said measurement and observation are performed simultaneously on the same sample and displayed simultaneously on the same screen, with microscopic observation of a physical phenomena selected from the group consisting of emulsification, coalescence, dilution, flocculation and decantation, whereby to establish correlations between:

(a) a variation of viscosity, particle size, homogeneity and texture characteristics, (b) conductivity or resistivity measurements characteristic of said variations, said device comprising, in combination:
    a Couette, Mooney or Cone-plane type analytical cell having a controlled shearing means;
a shearing microscopic observation means comprising:
    a microscope with a focusing system,
    a lighting system for the microscope, and
    a digital camera and associated image acquisition and processing electronics;
a light diffusion and/or turbidity monitoring system comprising:
    a laser source,
    a luminescent screen system and an optical system for obtaining a significant diffusion spectrum of particle size, and
    a digital camera and associated image acquisition and processing electronics;
a movement and to-and-fro system for horizontal adjustment and successive microscopic observations followed by light diffusion;
an automatic raising and lowering system for moving the rotor closer to the stator;
a temperature monitor and regulator;
a viscosity measurer;
a conductivity or dielectric constant measurer, comprising:
    a plurality of pairs of electrodes level with the inner surface of the analytical cell,
    a plurality of impedance monitors; and
    a computer for controlling said means and for performing, simultaneously, in real time, on the same sample:
        (a) microscopic observations and size or turbidity measurements by light diffusion equally on translucent diffusing or turbid products, the rotor being conical and the microscope and the diffusion device moving horizontally in order to select a suitable thickness for a satisfactory observation,
        (b) viscosity variation measurements, and
        (c) mean conductivity or resistivity variation measurements in two directions with respect to the shearing direction,
    said computer having logic for managing said means simultaneously and display in several windows of the screen:
        physical parameters and their variation during the experiment in the form of curves;
        static or dynamic microscopic observation and light diffusion windows; and
        instantaneous values of said measurements and historic curves for the entire experiment.

8. An automated device according to claim 7, and including, in combination:
a tank;
a mixing blade;
a fluid or gas injector or extractor;
said device further comprising a plurality of probes for positioning at varying positions in the tank, said probes comprising electrodes impedance measuring said probes being controlled by and the results being acquired, stored and displayed by said computer, wherein said means are combined and managed by application of the same functions whereby the device measures mean conductivity or dielectric constant at several points or levels of the tank, thus permitting the establishment of correlations between variation of physical parameters, observation of macroscopic phenomena and significant measurements.

9. An automated device according to claim 7, wherein said electrodes are connected to a rotary connector for permitting adjustment of polarity on said electrodes.

10. An automated device, according to claim 7, wherein said lighting system comprises a direct lighting system through the rotor shaft.

11. An automated device according to claim 7, wherein said lighting system comprises an episcopic lighting system, with the rotor being reflective.

* * * * *

UNITED STATES PATENT AND TRADEMARK OFFICE
CERTIFICATE OF CORRECTION

PATENT NO. : 6,535,796 B1  
DATED : March 18, 2003  
INVENTOR(S) : Sierro et al.

It is certified that error appears in the above-identified patent and that said Letters Patent is hereby corrected as shown below:

Column 18,
Line 66, after "characteristics," insert -- and; --

Signed and Sealed this

Eighteenth Day of May, 2004

JON W. DUDAS  
*Acting Director of the United States Patent and Trademark Office*